(12) United States Patent
Derkx et al.

(10) Patent No.: US 11,596,340 B2
(45) Date of Patent: Mar. 7, 2023

(54) METHODS AND SYSTEM FOR PROCESSING AN EMG SIGNAL

(71) Applicant: KONINKLIJKE PHILIPS N.V., Eindhoven (NL)

(72) Inventors: Rene Martinus Maria Derkx, Eindhoven (NL); Sandrine Magali Laure Devot, Cologne (DE)

(73) Assignee: Koninklijke Philips N.V., Eindhoven (NL)

(*) Notice: Subject to any disclaimer, the term of this patent is extended or adjusted under 35 U.S.C. 154(b) by 516 days.

(21) Appl. No.: 16/498,835

(22) PCT Filed: Mar. 30, 2018

(86) PCT No.: PCT/EP2018/058270
§ 371 (c)(1),
(2) Date: Sep. 27, 2019

(87) PCT Pub. No.: WO2018/178326
PCT Pub. Date: Oct. 4, 2018

(65) Prior Publication Data
US 2020/0100697 A1     Apr. 2, 2020

(30) Foreign Application Priority Data

Mar. 31, 2017   (EP) .................................... 17164181

(51) Int. Cl.
*A61B 5/021* (2006.01)
*A61B 5/316* (2021.01)
(Continued)

(52) U.S. Cl.
CPC ............... *A61B 5/316* (2021.01); *A61B 5/08* (2013.01); *A61B 5/352* (2021.01); *A61B 5/389* (2021.01);
(Continued)

(58) Field of Classification Search
CPC ......... A61B 5/0006; A61B 5/02; A61B 5/296; A61B 5/308; A61B 5/313; A61B 5/318;
(Continued)

(56) References Cited

U.S. PATENT DOCUMENTS

| 4,248,240 A | * | 2/1981 | van Eykern | ......... A61B 5/0809 600/484 |
| 5,524,632 A | | 6/1996 | Stein et al. | |

(Continued)

FOREIGN PATENT DOCUMENTS

| JP | 2002153435 A | 5/2002 |
| WO | 2005096924 A1 | 10/2005 |

OTHER PUBLICATIONS

Xue, Qiuzhen, Yu Hen Hu, and Willis J. Tompkins. "Neural-network-based adaptive matched filtering for QRS detection." IEEE Transactions on biomedical Engineering 39.4 (1992): 317-329. (Year: 1992).*

(Continued)

*Primary Examiner* — Navin Natnithithadha
*Assistant Examiner* — Meghan R Kumar
(74) *Attorney, Agent, or Firm* — Daniel H. Brean

(57) ABSTRACT

A method for generating a filtered EMG signal includes obtaining a combined signal, wherein the combined signal comprises an ECG signal and an EMG signal. A first high pass filter is applied to the combined signal and an ECG model signal is generated, based on the high pass filtered combined signal. The method further includes, generating a partially filtered EMG signal by subtracting the ECG model from the high pass filtered combined signal. A second high pass filter is then applied to the partially filtered EMG signal to generate a second EMG signal and to the ECG model signal to generate a second ECG model signal. A filtered (Continued)

EMG signal is generated based on the second EMG signal and the second ECG model by way of a gating technique.

19 Claims, 17 Drawing Sheets

(51) Int. Cl.
| | |
|---|---|
| *A61B 5/08* | (2006.01) |
| *A61B 5/00* | (2006.01) |
| *A61B 5/352* | (2021.01) |
| *A61B 5/389* | (2021.01) |
| *G16H 50/20* | (2018.01) |

(52) U.S. Cl.
CPC ............ *A61B 5/7203* (2013.01); *A61B 5/725* (2013.01); *G16H 50/20* (2018.01)

(58) Field of Classification Search
CPC ......... A61B 5/322; A61B 5/346; A61B 5/347; A61B 5/352; A61B 5/353; A61B 5/355; A61B 5/357; A61B 5/358; A61B 5/36; A61B 5/389; A61B 5/397; A61B 5/316; A61B 5/08; A61B 5/7203; A61B 5/725; G16H 50/20

See application file for complete search history.

(56) References Cited

U.S. PATENT DOCUMENTS

| | | | | |
|---|---|---|---|---|
| 5,792,069 | A | 8/1998 | Greenwald | |
| 6,411,843 | B1* | 6/2002 | Zarychta ................ | A61B 5/389 128/204.23 |
| 7,634,311 | B2 | 12/2009 | Blomberg et al. | |
| 11,077,310 | B1* | 8/2021 | Sullivan ................. | A61B 5/363 |
| 2009/0275850 | A1 | 11/2009 | Mehendale | |
| 2013/0310699 | A1* | 11/2013 | Hart ......................... | A61B 5/08 600/529 |
| 2014/0135879 | A1 | 5/2014 | Flint | |
| 2014/0142395 | A1* | 5/2014 | Sattler .................. | A61B 5/0205 600/300 |
| 2016/0113587 | A1* | 4/2016 | Kothe .................. | G06K 9/0057 600/559 |
| 2016/0228069 | A1* | 8/2016 | Derkx .................. | A61B 5/7221 |
| 2016/0278659 | A1 | 9/2016 | Kaib | |
| 2018/0020928 | A1 | 1/2018 | Hart et al. | |
| 2018/0235503 | A1* | 8/2018 | Derkx .................. | A61B 5/6833 |
| 2020/0008299 | A1* | 1/2020 | Tran ...................... | H05K 1/0286 |

OTHER PUBLICATIONS

Censi, Federica, et al. "Effect of high-pass filtering on ECG signal on the analysis of patients prone to atrial fibrillation." Annali dell'Istituto Superiore di Sanita 45 (2009): 427-431. (Year: 2009).*

Drake, Janessa DM, and Jack P. Callaghan. "Elimination of electrocardiogram contamination from electromyogram signals: An evaluation of currently used removal techniques." Journal of electromyography and kinesiology 16.2 (2006): 175-187. (Year: 2006).*

Drake, J.D.M. et al., "Elimination of electrocardiogram contamination from electromyogram signals: an evaluation of currently used removal techniques", Journal of Electromyography and Kinesiology, Elsevier, Amsterdam, NL, vol. 16, No. 2, Apr. 1, 2006, pp. 175-187.

International Search Report for PCT/EP2018/058270 dated Mar. 30, 2018.

Murphy, P.B. et al., "Neural respiratory drive as a physiological biomarker to monitor change during acute exacerbations of COPD", Thorax 2010, May 19, 2011 (published online).

Breslin, E.H., et al., "Respiratory muscle function in patients with chronic obstructive pulmonary disease", Heart & Lung, vol. 24, No. 4, Jul./Aug. 1996, pp. 271-285.

Duiverman, M.L. et.al., "Reproducibility and responsiveness of a non-invsaive EMG technique of the respiratory muscles in COPD patients and in healthy subjects", J. Appl. Physiol., Dec. 5, 2003.

De Troyer, A. et al., "Respiratory Action of the Intercostal Muscles", Physiol Rev, vol. 85, pp. 717-756, 2005.

Han, J.N. et al., "Respiratory function of the rib cage muscles," Eur Respir J, vol. 6, pp. 722-728, 1993.

Bartolo, A., et al., "Analysis of diaphragm EMG signals: comparison of gating vs. subtraction for removal of ECG contamination". Journal of applied physiology, 80(6), Jun. 1996, Abstract.

Pan, J. et al., "A real-time QRS detection algorithm", IEEE Trans. Biomed. Eng., vol. 32, No. 3, pp. 230-236, 1985.

Eykem Van, L.A. et al. Two similar averages for respiratory muscle activity, Letter to editor, J. Appl. Physiology 90:2014-2015, 2001.

Giuliani, C. et.al., "T-wave frequency content evaluation in healthy subjects and patients affected by myocardial infraction", Signal Processing: New research, Nova Science Publishers, 2013, pp. 79-93.

* cited by examiner

METHODS AND SYSTEM FOR PROCESSING AN EMG SIGNAL

CROSS-REFERENCE TO PRIOR APPLICATIONS

This application claims the priority benefit under 35 U.S.C. § 371 of International Patent Application No. PCT/EP2018/058270, filed on Mar. 30, 2018, which claims the priority benefit of European Patent Application No. 17164181.4 filed on Mar. 31, 2017, the contents of which are herein incorporated by reference.

FIELD OF THE INVENTION

This invention relates to the field of signal processing, and more specifically to the field of electromyogram (EMG) signal processing.

BACKGROUND OF THE INVENTION

In patients with chronic obstructive pulmonary disease (COPD) and other respiratory diseases, the assessment of the parasternal muscle activity measured from surface EMGs can be used to estimate the intensity, timing and duration of patient respiratory effort. This can serve as an indicator of the balance between respiratory muscle load and respiratory muscle capacity. The maximum EMG level that occurs during inhalation is related to the neural respiratory drive (NRD). During lung hyperinflation, as observed in COPD patients during acute exacerbation, there is a change in the balance between respiratory muscle load and capacity, which is reflected in the neural respiratory drive. A lower capacity and higher load result in an increased NRD. The maximum power of EMG signals measured from respiratory muscles, for example from parasternal muscles at the $2^{nd}$ intercostal space or from the diaphragm at the abdomen, via EMG electrodes, during inhalation can be used as an indicator of the deterioration or improvement of the patient. This may also be used as a predictor of hospital readmission after discharge.

Before the inspiratory EMG activity can be measured, the ECG contamination that is present in the differential measurement must be removed. When measuring EMG signals in COPD patients during quiet breathing and/or when performing forced maximum volitional inspirations, referred to as sniffs, the EMG energy can come close, or even exceed, the ECG energy. This leads bad signal to noise ratio (SNR) conditions, causing a problem in the ECG removal as R-peaks, within the ECG signals, may be erroneously detected in such high energy EMG regions. A falsely detected R-peak can either lead to: under-estimated EMG levels, because a large EMG peak is detected as an R-peak; or over-estimated EMG levels, because an R-peak is not detected.

There is therefore a need for a method of reliably removing ECG contamination in poor SNR conditions from an EMG signal, and without requiring significant additional hardware.

SUMMARY OF THE INVENTION

The invention is defined by the claims.

According to examples in accordance with an aspect of the invention, there is provided a method for generating a filtered EMG signal, the method comprising:

obtaining a combined signal, wherein the combined signal comprises an ECG signal and an EMG signal;
applying a first high pass filter to the combined signal;
generating an ECG model signal based on the high pass filtered combined signal;
generating a first EMG signal based on at least one of the ECG model signal and the high pass filtered combined signal;
applying a second high pass filter to the first EMG signal to generate a second EMG signal and to the ECG model signal to generate a second ECG model signal; and
generating a filtered EMG signal based on the second EMG signal and the second ECG model by way of a gating technique.

This method produces an EMG signal substantially free of ECG contamination signals in poor SNR conditions where the EMG signal dominates over the ECG signal. By applying a first high pass filter, it is possible to remove the noise from the signal, whilst preserving ECG energy to be used in the generation of the ECG model signal. The ECG model signal acts to estimate the ECG component of the high pass filtered combined signal.

By generating a first EMG signal, which is preferably a partially filtered EMG signal, based on the high pass filtered combined signal and/or the ECG model; it is possible to obtain an EMG signal with substantially less ECG contamination. The second high pass filter may then be applied to further remove the ECG energy that, whilst useful for the generation of the ECG model signal, would have a negative effect on the gating technique. In this way, it is possible to preserve ECG energy to be used in the generation of the ECG model signal, whilst preventing said ECG energy from disrupting the gating technique. The second high pass filter is also applied to the ECG model signal to produce a second ECG model signal that may be used to control the gating technique.

In an embodiment, the first high pass filter has a cutoff frequency of less than 20 Hz, for example less than or equal to 5 Hz.

As is well known, each pulse of an ECG signal comprises a series of peaks and troughs identified as PQRST components. The P-wave, the so-called QRS complex and the T-wave represent the electrical activity in the heart on the ECG. The P-wave represents the depolarization of the right and left atria. The QRS complex follows the P wave and depicts the activation of the right and left ventricles. The T wave represents the repolarization of the ventricles. The Q-T interval represents the time necessary for ventricular depolarization and repolarization.

The dominant pulse is the R signal, and hence this is most suitable for determining the ECG pulse timing and hence also for a gating approach. However, the T-wave also carries significant energy and hence is also of use in generating an ECG signal model.

By applying a high pass filter with a cutoff frequency of less than 20 Hz, for example less than or equal to 5 Hz, it is possible to preserve a substantial amount of energy of the ECG signal. In this way, the generating of the ECG model signal may be improved in the case of poor SNR conditions. In turn, this may lead to a more accurate gating technique and hence a more accurate filtered EMG signal.

In an embodiment, the second high pass filter has a cutoff frequency of greater than 15 Hz, for example greater than or equal to 20 Hz.

In this way, the second high pass filter can filter out the ECG energy preserved by the first high pass filter before the gating technique is applied to the signals. More specifically, the second high pass filter can remove the T-wave energy and a substantial amount of the QRS complex energy from the ECG signal. By including this second high pass filter, it is possible to prevent the gating technique from gating out too much energy and to only gate out a small portion of energy belonging to the residual QRS complex that remains after applying the second high pass filter.

In an arrangement, the generating of the ECG model signal comprises:

generating an enhanced ECG signal by applying a matched filter to the high pass filtered combined signal, wherein the matched filter uses an ECG template;

identifying peaks in the enhanced ECG signal;

identifying fiducial points in the high pass filtered combined signal based on the peaks in the enhanced ECG signal; and generating an ECG model signal based on the high pass filtered combined signal and the fiducial points.

By identifying fiducial points of the ECG signal within the high pass filtered combined signal, it is possible to generate the ECG model signal by averaging multiple ECG cycles using the fiducial points as a time-reference to obtain an ECG template. The ECG template and the identified fiducial points may then be used to estimate the ECG model signal. By using the ECG model signal, it is possible to remove the ECG contamination from the high pass filtered combined signal, resulting in a clearer filtered EMG signal. The matched filter makes use of the ECG template, resembling a waveform of a single ECG cycle, in order to identify the fiducial points of the ECG signal within the high pass filtered combined signal.

In a further arrangement, the fiducial points comprise R-peaks.

R-peaks are the most prominent fiducial point of an ECG signal. By identifying R-peaks as fiducial points of the ECG signal within the high pass filtered combined signal, multiple ECG cycles can be used to recover the average ECG signal shape, which may then be used for the generation of the ECG model signal. In this way, the ECG model signal can be a closer representation of the ECG signal within the original combined signal, thereby resulting in a more accurate filtered EMG signal.

In a yet further arrangement, the generating of the ECG model signal further comprises tapering each ECG cycle in the ECG model signal.

This tapering prevents the appearance of discontinuities between subsequent ECG cycles in the ECG model signal, which would lead to high-frequency disturbances in the second EMG signal and the second ECG model signal. For example, the tapering can be adapted to taper the ECG model signal values that lie between two subsequent ECG cycles toward zero.

In some arrangements, the generating of the ECG model signal further comprises:

computing an ECG template using a single ECG cycle of the ECG model signal; and providing the computed ECG template to the matched filter.

By providing the ECG template to the matched filter, the matched filter can filter the high pass filtered combined signal to produce an enhanced ECG signal with more clearly defined peaks relating to the fiducial points in the ECG signal within the high pass filtered combined signal. In this way, rather than using a generic ECG signal template, after the first ECG template is generated by using the ECG model signal, an accurate ECG template may be used on a per measurement basis.

In an embodiment, the gating technique comprises:

computing the root mean square, RMS, of the ECG model signal;

computing a binary gating signal based on the RMS of the ECG model signal; and gating the second EMG signal using the binary gating signal.

In practice, the subtraction of the ECG model signal from the high pass filtered combined signal may not fully remove all of the ECG signals from the high pass filtered combined signal and the second EMG signal may contain some residual ECG contamination. This may be removed by way of the gating technique. By computing the binary gating signal based on the RMS of the ECG model signal and using it to gate the second EMG signal, it is possible to remove the residual EMG signals.

In some embodiments, the method further comprises generating a continuous RMS of the filtered EMG signal, wherein the generating of the continuous RMS of the filtered EMG signal comprises:

estimating a signal level of a non-gated region close to a gate boundary of the filtered EMG signal;

generating a continuous filtered EMG signal by interpolating values in a gated region of the filtered EMG signal based on the estimated signal levels; and computing the RMS of the continuous filtered EMG signal.

The filtered EMG signal, produced by way of the gating technique, will include sections of zero signal amplitude, referred to as gated regions. By reconstructing these gated regions, it is possible to produce a continuous filtered EMG signal that may be used in further analysis. The continuous RMS of the filtered EMG signal may then be used to compute a clinical parameter of the user. The clinical EMG parameter may then be used to compute various metrics relating to the respiratory function of the user, for example neural respiratory drive (NRD).

In an arrangement, the generating of the first (partially filtered) EMG signal comprises subtracting the ECG model signal from the high pass filtered combined signal.

By subtracting the ECG model signal from the high pass filtered combined signal, a large proportion of the ECG contamination in the high pass filtered combined signal is removed.

In some designs, the method further comprises, after applying the first high pass filter, buffering the high pass filtered combined signal.

In further designs, the buffering is performed over a time period of between 30 seconds and 5 minutes, for example over a time period of 1 minute.

By performing buffering on the high pass filtered combined signal, it is possible to collect signal samples over a given time window, such as over one minute. In this way, the generation of the ECG model signal may be done with greater ease. The buffering may make use of a sliding window so that there is overlap between successive sections of buffered data.

According to examples in accordance with an aspect of the invention, there is provided a computer program comprising computer program code means which is adapted, when said computer is run on a computer, to implement the method described above.

According to examples in accordance with an aspect of the invention, there is provided an EMG measurement system comprising:

an EMG electrode adapted to measure the combined signal;
  a controller, wherein the controller is adapted to:
    obtain a combined signal, wherein the combined signal comprises an ECG signal and an EMG signal;
    apply a first high pass filter to the combined signal;
    generate an ECG model signal based on the high pass filtered combined signal;
    generate a first EMG signal based on at least one of the high pass filtered combined signal and the ECG model signal;
    apply a second high pass filter to the first EMG signal to generate a second EMG signal and to the ECG model signal to generate a second ECG model signal; and
    generate a filtered EMG signal based on the second EMG signal and the second ECG model by way of a gating technique; and
  a signal output device for outputting the filtered EMG signal.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a method for generating a filtered EMG signal. The method includes obtaining a combined signal, wherein the combined signal comprises an ECG signal and an EMG signal. A first high pass filter is applied to the combined signal and an ECG model signal is generated, based on the high pass filtered combined signal. The method further includes, generating a partially filtered EMG signal by subtracting the ECG model signal from the high pass filtered combined signal. A second high pass filter is then applied to the partially filtered EMG signal to generate a second EMG signal and to the ECG model signal to generate a second ECG model signal. A filtered EMG signal is generated based on the second EMG signal and the second ECG model by way of a gating technique.

Figure 1:
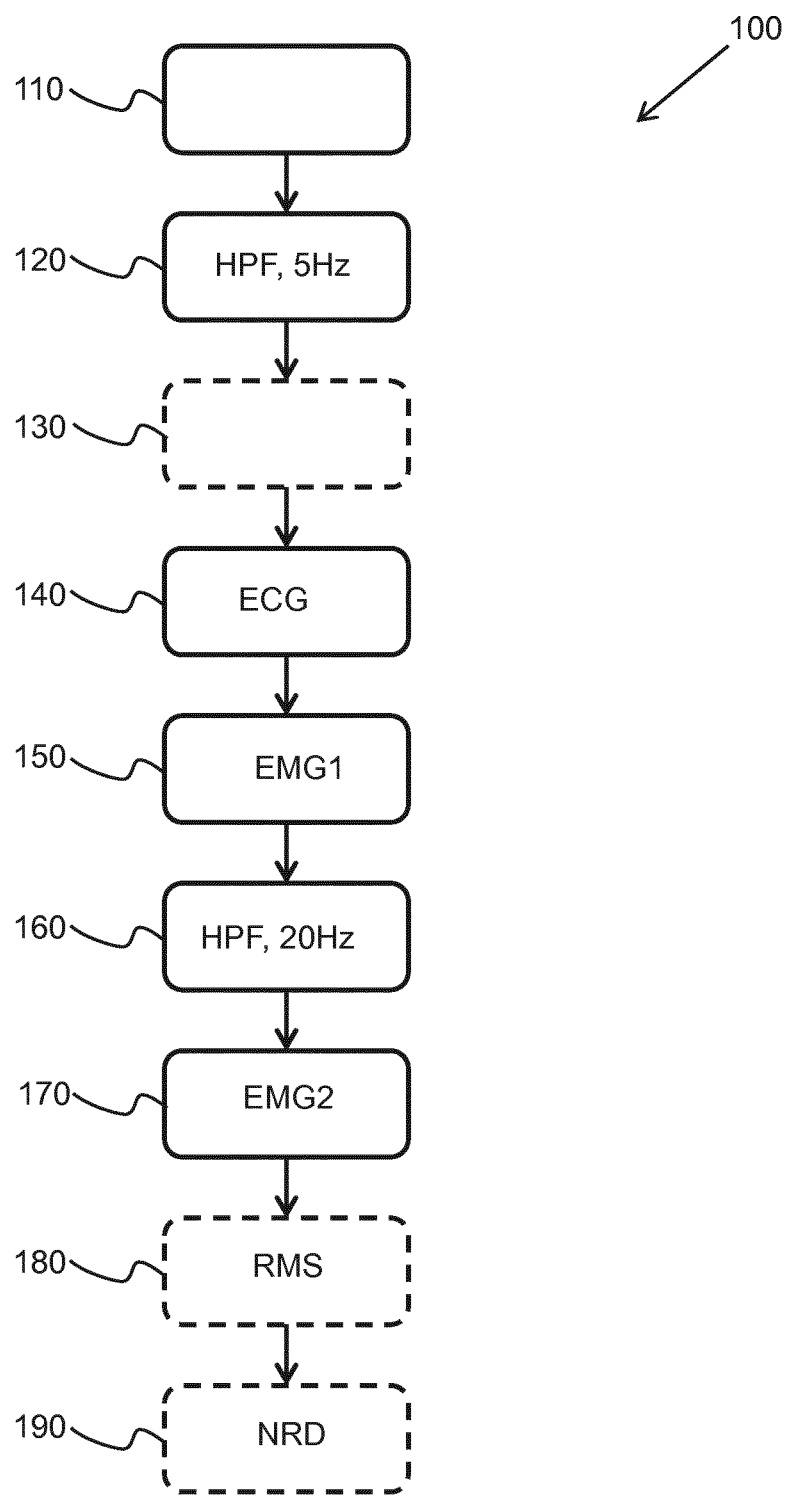
FIG. 1 shows a method of the invention.

FIG. 1 shows a method 100 of generating a filtered EMG signal.

In step 110, a combined signal is obtained, wherein the combined signal comprises an ECG signal and an EMG signal.

An EMG signal measured, for example at the $2^{nd}$ intercostal space parasternal muscles, is typically heavily contaminated by ECG signals, which often have a higher energy than the EMG signal itself.

In some cases, the EMG signal is higher in energy than the ECG energy. This can happen when the user performs maximum voluntarily inspiratory maneuvers, known as sniffs. In these situations, it can be difficult to remove the ECG contamination due to the poor signal to noise ratio of the combined signal. In order to identify and remove the ECG signals from the combined signal, several processing steps are performed.

In step 120, a first high pass filter is applied to the combined signal.

The first high pass filter may have a cutoff frequency of less than 20 Hz, for example less than or equal to 5 Hz. The first high pass filter is adapted to remove noise and motion artifacts from the combined signal, whilst preserving the energy of the ECG signal.

A cutoff frequency of 5 Hz provides a good balance between removing noise and motion artifacts, such as baseline shifts, and preserving the energy of the ECG signal, including the T-waves; whereas, a high pass filter with a cutoff frequency of 1 Hz, whilst preserving more of the ECG signal, is far more susceptible to motion artifacts. A cutoff frequency of 20 Hz removes motion artifacts and the T-waves, but preserves the energy of the QRS complex in the ECG signal.

In step 130, the high pass filtered combined signal undergoes buffering.

The buffering may be performed over a period of one minute. Alternatively, the buffering may occur for longer than one minute, for example two or three minutes, or for less than one minute, for example 30 seconds.

The buffering period may be used to collect samples of the high pass filtered combined signal in a given time window. In some cases then buffering period may overlap with a previous buffering period from a previous cycle of the method 100. This may enable a sliding window, for example of 10 seconds, to be implemented for each method cycle.

In step 140, an ECG model is generated based on the high pass filtered combined signal.

An enhanced ECG signal is generated by applying a matched filter to the high pass filtered combined signal, wherein the matched filter uses an ECG template. The matched filter works by using a template signal, such as the ECG template, to recognize and isolate a similar shape within an input signal, such as the high pass filtered combined signal.

For the first iteration of the method, the ECG template may be a generic single cycle of the ECG signal; however, after an ECG model signal has been generated from the high pass filtered combined signal, a single cycle of the ECG model signal may then be used as the ECG template for subsequent iterations of the method. The ECG template may be continually updated using the latest ECG model signal, thereby improving the accuracy of the matched filter. Alternatively, the initial ECG template may be a bandpass filter with 20 (lower) and 40 Hz (upper) cutoff frequencies to enhance the ECG at the output of the matched filter and minimize the EMG influences.

Following the step of generating the enhanced ECG signal from the combined signal, peaks of the enhanced ECG signal are identified and are fine-tuned to the high pass filtered combined signal to act as fiducial points of the high pass filtered combined signal for generating the ECG model signal. The most prominent fiducial point of an ECG signal is the R-peak as it typically has the highest amplitude with a sharp peak. The R-peaks may have either positive or negative peak-values.

Finally, an ECG model signal is generated based on the high pass filtered combined signal and the fiducial points. The fiducial points may be tuned, meaning slightly aligned in time, to the high pass filtered combined signal. For example, the if peaks of the enhanced ECG signal do not match the peaks of the high pass filtered signal, they may be shifted by, at a maximum, 5 ms.

In step 150, a partially filtered EMG signal is generated based on at least one of the ECG model signal and the high pass filtered combined signal. For example, the ECG model signal may be subtracted from the high pass filtered combined signal. By subtracting the ECG model signal from the high pass filtered combined signal, the majority of the ECG contamination is eliminated, leaving a more accurate EMG signal.

In step 160, two instances of a second high pass filter are applied to the partially filtered EMG signal to generate a second EMG signal and to the ECG model signal to generate a second ECG model signal. The two instances of the second high pass filter have equal cutoff frequencies, which may be greater than 15 Hz, for example greater than or equal to 20 Hz.

When applying a gating technique to the second EMG signal in subsequent steps, it is beneficial to remove the ECG energy that relates to the T-waves, as the T-waves are not localized in time and the gating technique will remove too much energy from the second EMG signal. In order to prevent the gating technique from gating too much energy out of the partially filtered EMG signal due to the T-Wave energy within the ECG model signal, the T-wave energy may be filtered out by the second high pass filter. As the T-wave energy lies in the frequency range of 2 to 10 Hz, a second high pass filter with a cutoff frequency of 20 Hz will remove any T-wave energy from the ECG model and partially filtered EMG model.

Alternatively, it might be beneficial to have an even larger cutoff frequency of the second high pass filter, for example a cutoff frequency of 100 Hz. This larger cutoff frequency will not only remove the T-wave energy from the ECG model signal and the partially filtered EMG signal, but also a large portion of the QRS complex energy from the ECG model signal and the partially filtered EMG signal. As a result, the residual QRS-complexes in the second EMG signal are temporally very narrow and the gating technique will therefore gate out only a small portion of the energy. This leads to only a small portion of gated parts in the filtered EMG signal.

In step 170, a filtered EMG signal is generated by applying a gating technique to the second EMG signal by using the second ECG model signal as a control signal for the gating technique.

A gating technique may be used to further the amount of cancellation obtained by the subtraction of the ECG model signal. For the gating technique, the RMS of the second ECG model signal is computed as:

$$ECG\_model\_RMS(k)=sqrt[avg[(ECG')^2(k)]],$$

where: ECG_model_RMS(k) is the RMS of the second ECG model signal, ECG'; k is the sample index; the operator avg[.] computes a moving average of, for example, 50 ms; and the operator sqrt[.] computes the square-root. For a reduction of the residual ECG contamination in the second EMG signal, a binary gating signal, gate(k), is computed as:

$$gate(k)=ECG\_model\_RMS(k)<[median(ECG\_model\_RMS)*gate\_thresh],$$

where: median(ECG_model_RMS) is the median RMS value of the second ECG model signal within a given window, such as 1 minute; and the parameter gate_thresh may be used as an additional factor to fine-tune the sensitivity of the gating technique. Typical values for gate_thresh may be between 1 and 2. As the second ECG model signal no longer includes T-wave energy, the second ECG model signal contains a significant amount of low values. By using the median operator on the second ECG model signal to define the threshold, the gate may effectively remove the residual ECG energy in the second EMG signal when applying the gate to the second EMG signal.

This means that for high RMS values of the ECG model signal (with the RMS higher than the median of the RMS values of the ECG model signal), the signal gate(k) is equal to zero and the residual ECG energy in the second EMG signal is removed.

With the binary gating signal, gate(k), the second EMG signal may be gated as follows:

$$EMG''(k)=EMG'(k)*gate(k),$$

where EMG"(k) is the filtered EMG signal. The filtered EMG signal is an elementwise multiplication of the second EMG signal and the gating signal. The implementation of the gating technique as described above is only an example of how the gating may be performed using the ECG model signal.

In step 180, a continuous RMS of the filtered EMG signal may be generated.

A simple RMS calculation may be performed on the filtered EMG signal; however, due to the gating technique, the RMS of the filtered EMG signal will not be continuous. The gated regions of the filtered EMG signal may be interpolated by first estimating the signal levels of the non-gated regions close to the gate boundaries of the filtered EMG signal. A continuous filtered EMG signal may then be computed by interpolating the values in the gated regions of the filtered EMG signal by using the estimated signal levels at the boundaries of the gated regions. Next, the continuous RMS signal may then be constructed from the continuous filtered EMG signal.

In step 190, a clinical EMG parameter, such as the NRD, is generated based on the continuous RMS of the continuous filtered EMG signal. The clinical parameter may be generated on the continuous RMS of the continuous filtered EMG signal in combination with one or more physiological signals. For example, when computing the NRD, an external respiration sensor, such as a nasal cannula, may be used in conjunction with the continuous RMS signal to detect inspiratory phases more robustly. For example, the maximum RMS value of the EMG signal that occurs during inhalation may be determined.

Figure 2:
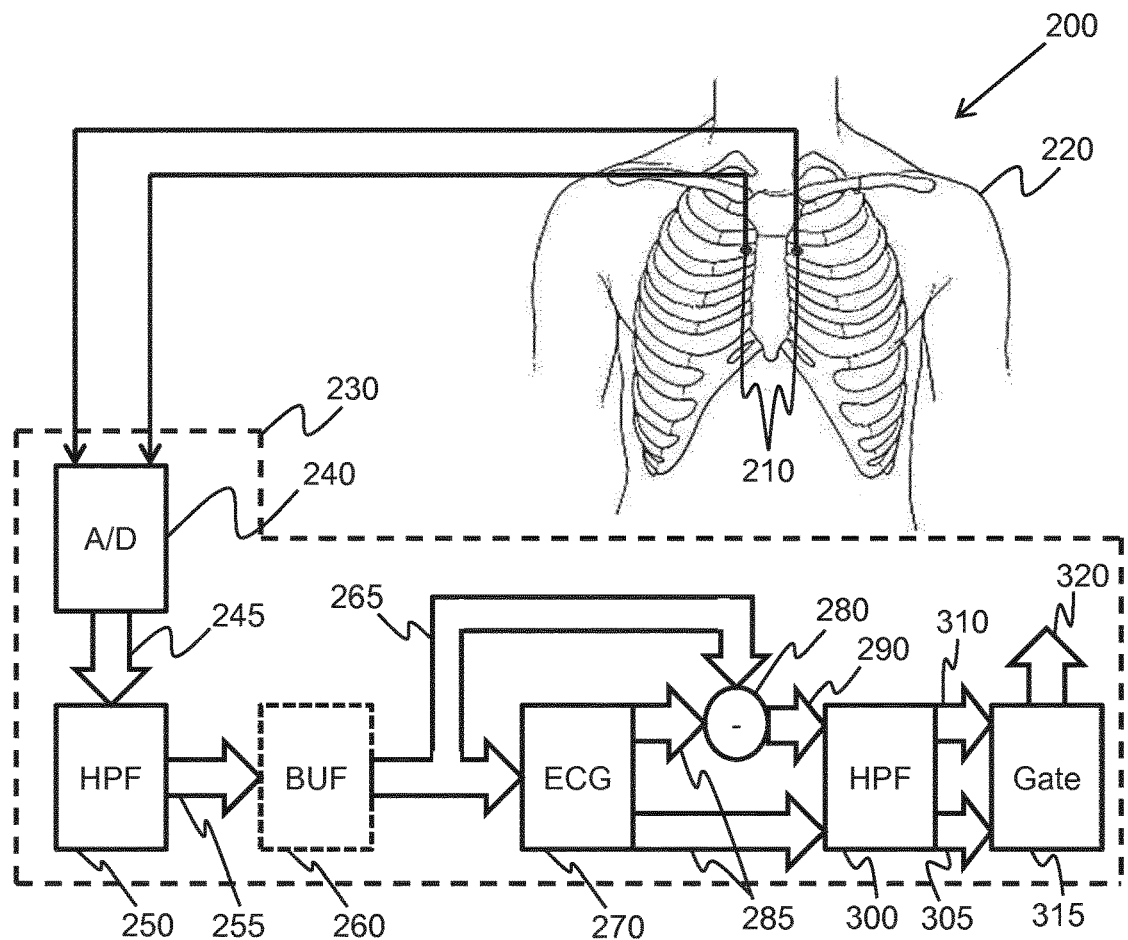
FIG. 2 shows a system for generating a filtered EMG signal.

FIG. 2 shows a system for generating a filtered EMG signal.

Two EMG electrodes 210 are provided at the second intercostal space of a user 220, with one electrode located at either side of the sternum. Alternatively, the electrodes may be located at the upper abdomen of the user, thereby measuring EMG signals from the diaphragm. The electrodes may be provided in a single patch to be administered to the user, or individually.

The EMG electrodes detect a combined signal, containing EMG and ECG signals of the user, which may then be provided to a signal processing unit 230. The signal processing unit may contain an analogue to digital converter 240, which is adapted to convert the analogue combined signal to a digital form. In this way, the combined signal may be processed by a digital system.

The digitized combined signal 245 may then be provided to the first high pass filter 250, which may, for example, have a cutoff frequency of 5 Hz. The high pass filtered combined signal 255 may then undergo buffering 260. The buffered high pass filtered combined signal 265 may then be split along two channels. The first channel provides the buffered high pass filtered combined signal to the ECG model signal generation unit 270, which is described in more detail with reference to FIG. 3, and the second channel provides the buffered high pass filtered combined signal to a subtraction unit 280.

The ECG model signal generation unit 270 generates the ECG model signal 285, which is output from the unit along two channels. The first channel provides the ECG model signal to the subtraction unit 280, which may then subtract the ECG model signal from the buffered high pass filtered combined signal, thereby producing a partially filtered EMG signal 290. The partially filtered EMG signal is then provided to the first instance of the second high pass filter 300. The second channel provides the ECG model signal directly to the second instance of the second high pass filter.

The second high pass filter, for example with a cutoff frequency of 20 Hz, produces a second EMG signal 305 and a second ECG model 310, which are both provided to a gating unit 315. The gating unit implements the gating technique, for example the gating technique described above, in order to produce a filtered EMG signal 320.

Figure 3:
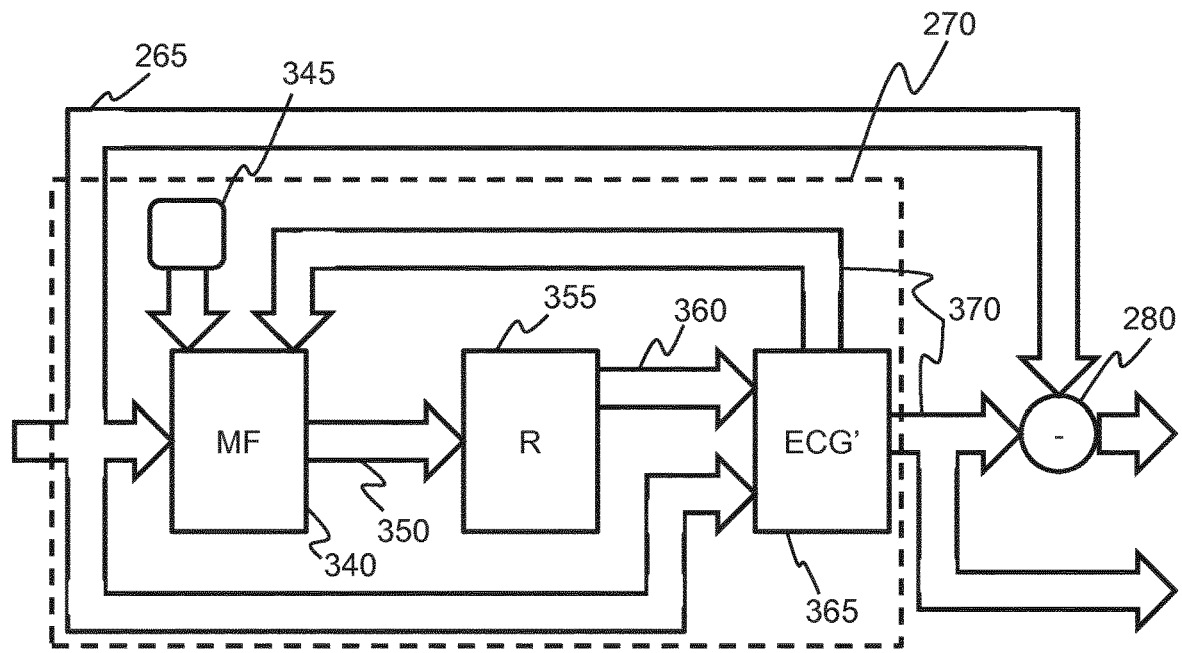
FIG. 3 shows a section of the system of FIG. 2 in more detail.

FIG. 3 shows a detailed view of the ECG model signal generation unit 270 of the system shown in FIG. 2.

The buffered signal 265 is provided to the ECG model signal generation unit 270 and the subtraction unit 280, as before. Within the ECG model signal generation unit, the buffered high pass filtered signal is divided into two channels, the first of which provides the buffered high pass filtered signal to the matched filter 340. The matched filter may make use of an initial ECG template 345, as described above, in order to generate an enhanced ECG signal 350 from the buffered high pass filtered signal.

The enhanced ECG signal is then provided to a peak detection unit 355, which is adapted to detect peaks, such as peaks relating to R-peaks of the ECG signal within the high pass filtered combined signal 265, within the enhanced ECG signal. These peaks 360 are supplied to the ECG model signal generator 365. Together with the high pass filtered combined signal 265, the peaks 360 are fine-tuned to act as fiducial points of the ECG signal within the high pass filtered combined signal 265 for constructing an ECG model signal 370. A single ECG cycle of the ECG model signal may then be provided to the matched filter 340 to act as an ECG template, thereby increasing the accuracy of the matched filter. Alternatively, the ECG template may be combined with the initial EMG template for use by the matched filter. The ECG model signal is then output from the ECG model signal generation unit 270 and the method continues as described above. By preserving the T-wave energy and QRS complex energy, the ECG template taken from the ECG model signal may more accurately represent the ECG signal within the high pass filtered combined signal.

Figure 4A:
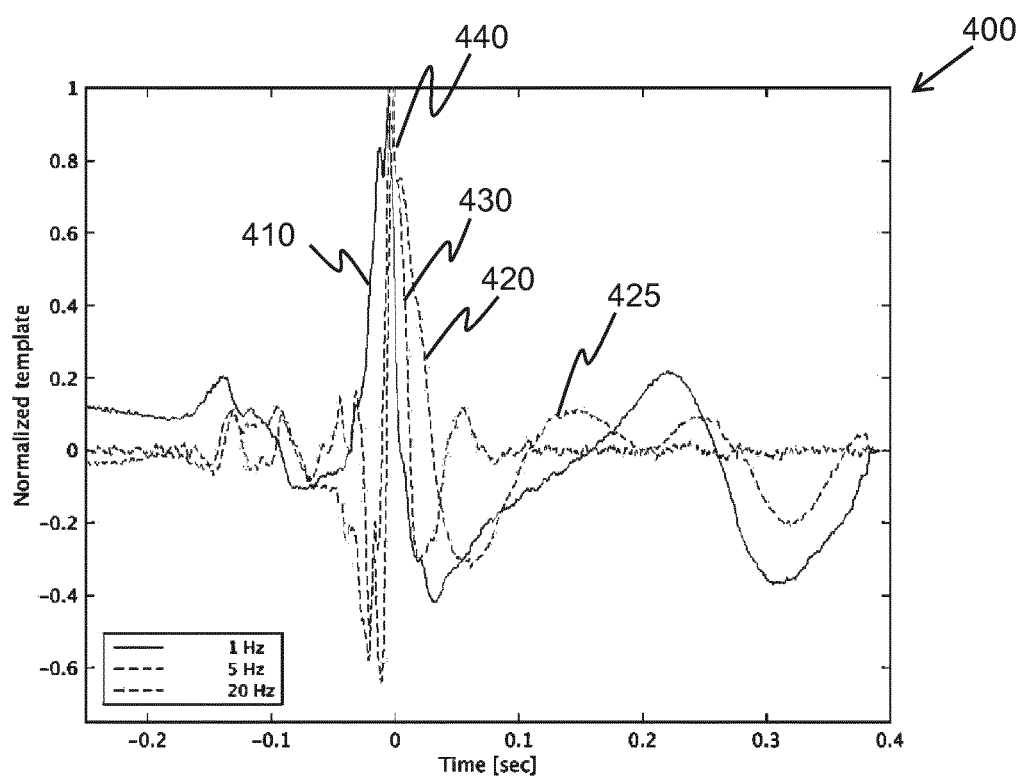
FIGS. 4A to 4D show three ECG templates for three different first high pass filter cutoff frequencies.

FIG. 4A shows a graph 400 of signal amplitude, normalized against R-peak amplitude, against time of three examples of ECG templates for three different cutoff frequencies of the first high pass filter. The first plot 410 shows the ECG template for a first high pass filter with a cutoff frequency of 1 Hz. As can be seen from the graph, the ECG template preserved the majority of the ECG energy, including the T-wave; however, this ECG template is very susceptible to noise and motion artifacts.

The second plot 420 shows an ECG template for a first high pass filter with a cutoff frequency of 5 Hz. In this case, less ECG energy is preserved; however, the T-wave 425 of the ECG signal, in addition to the R-peak, is still clearly visible. In this way, still a significant amount of energy of the ECG signal may be preserved, whilst also filtering out the majority of the noise and motion artifacts from the combined signal. Finally, the third plot 430 shows an ECG template for a first high pass filter with a cutoff frequency of 20 Hz. Compared to the first and second plots, all the energy of the T-wave has been removed by the first high pass filter. Hence, the energy of the T-wave can no longer be exploited in the matched filter 340.

Figure 4B:
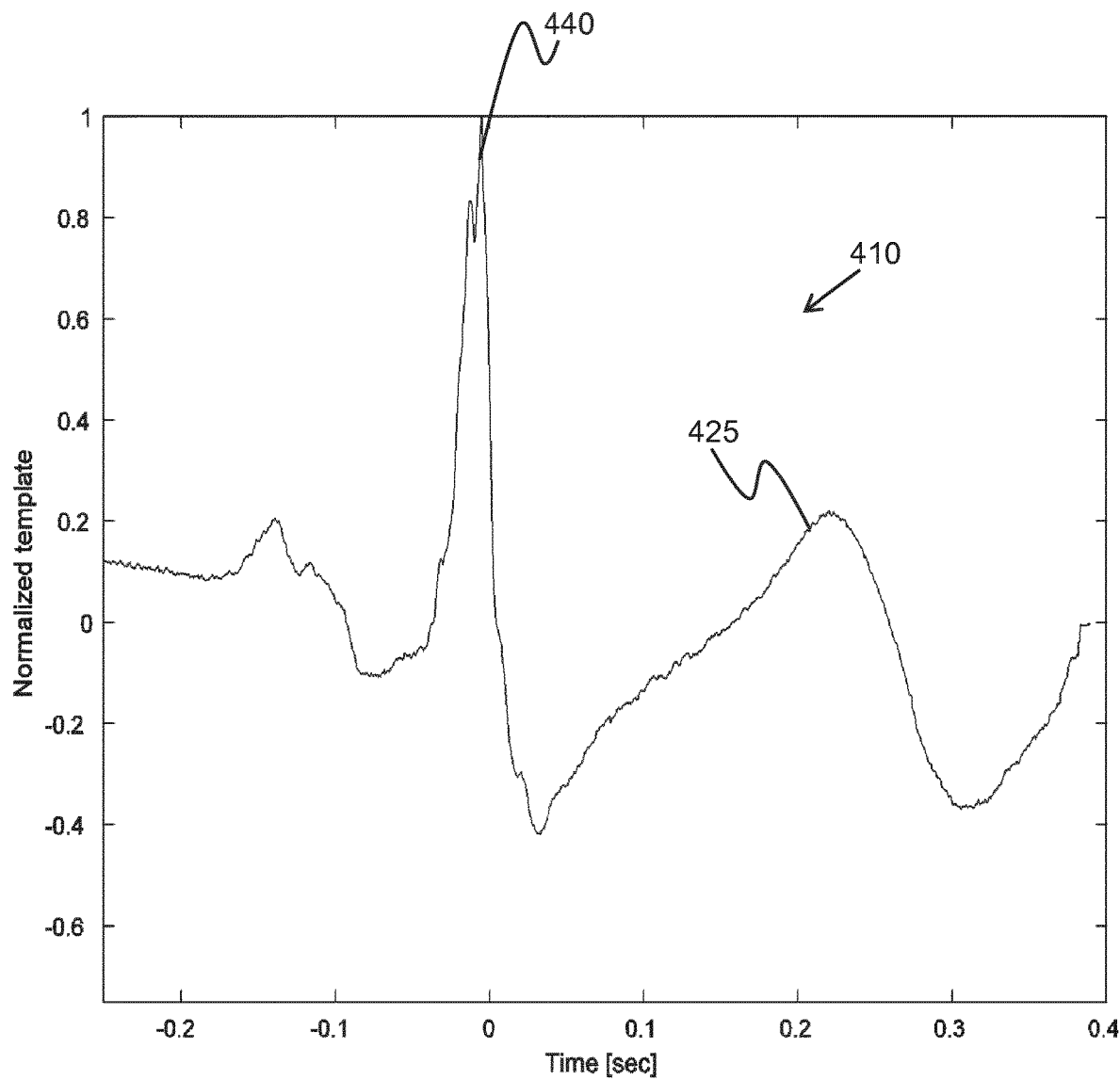
Figure 4C:
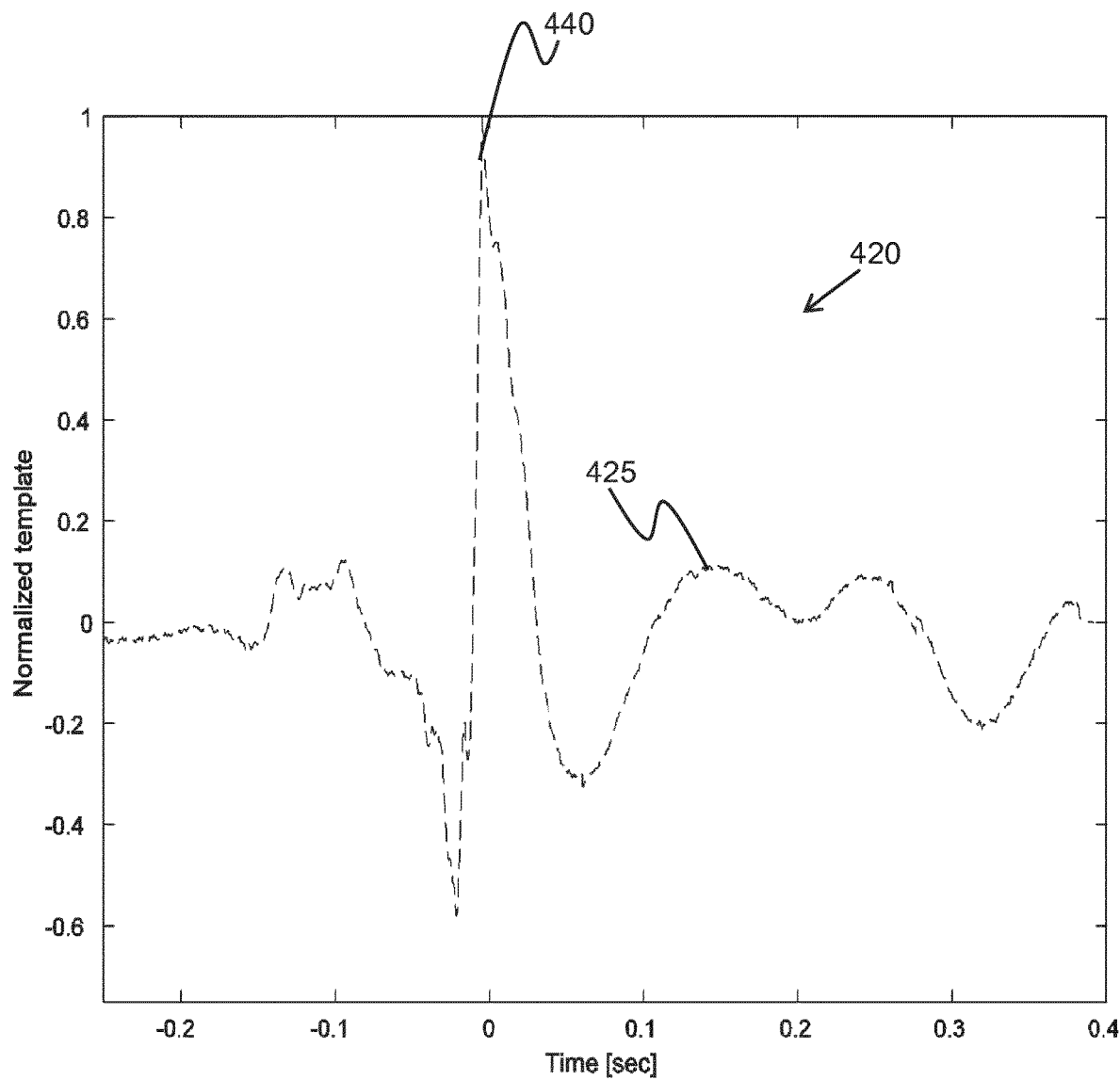
Figure 4D:
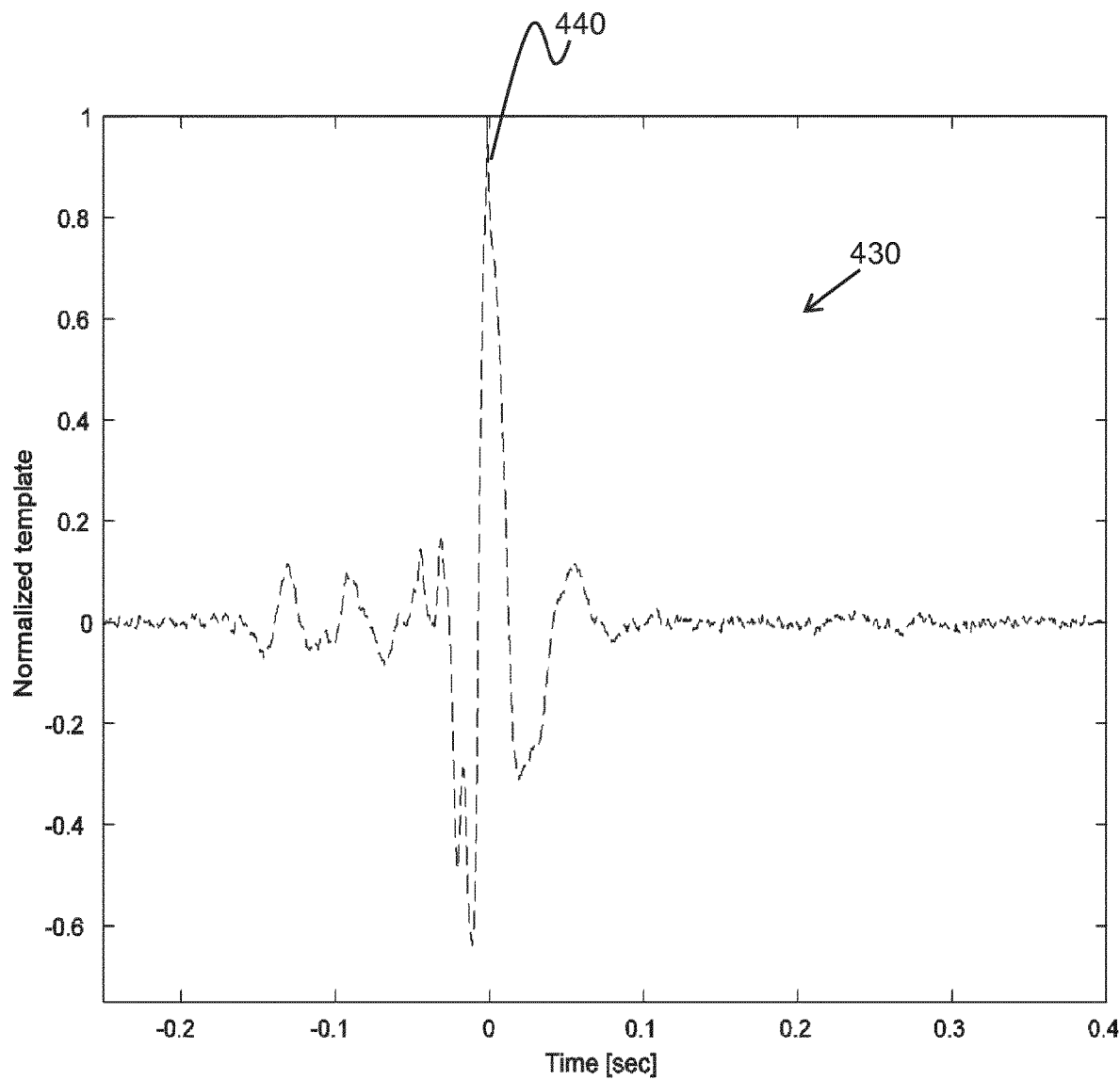

For the purposes of clarity, FIGS. 4B to 4D show the first 410, second 420 and third 430 plots of FIG. 4A, respectively, on separate graphs. From FIGS. 4B to 4D, it is clear to see that both the R-peak 440 and T-wave 425 of the ECG template are preserved by first high pass filters with cutoff frequencies of 1 or 5 Hz, as shown in FIGS. 4B and 4C; whereas, the T-wave has been removed by the first high pass filter with a cutoff frequency of 20 Hz, as shown in FIG. 4D.

Figure 5A:
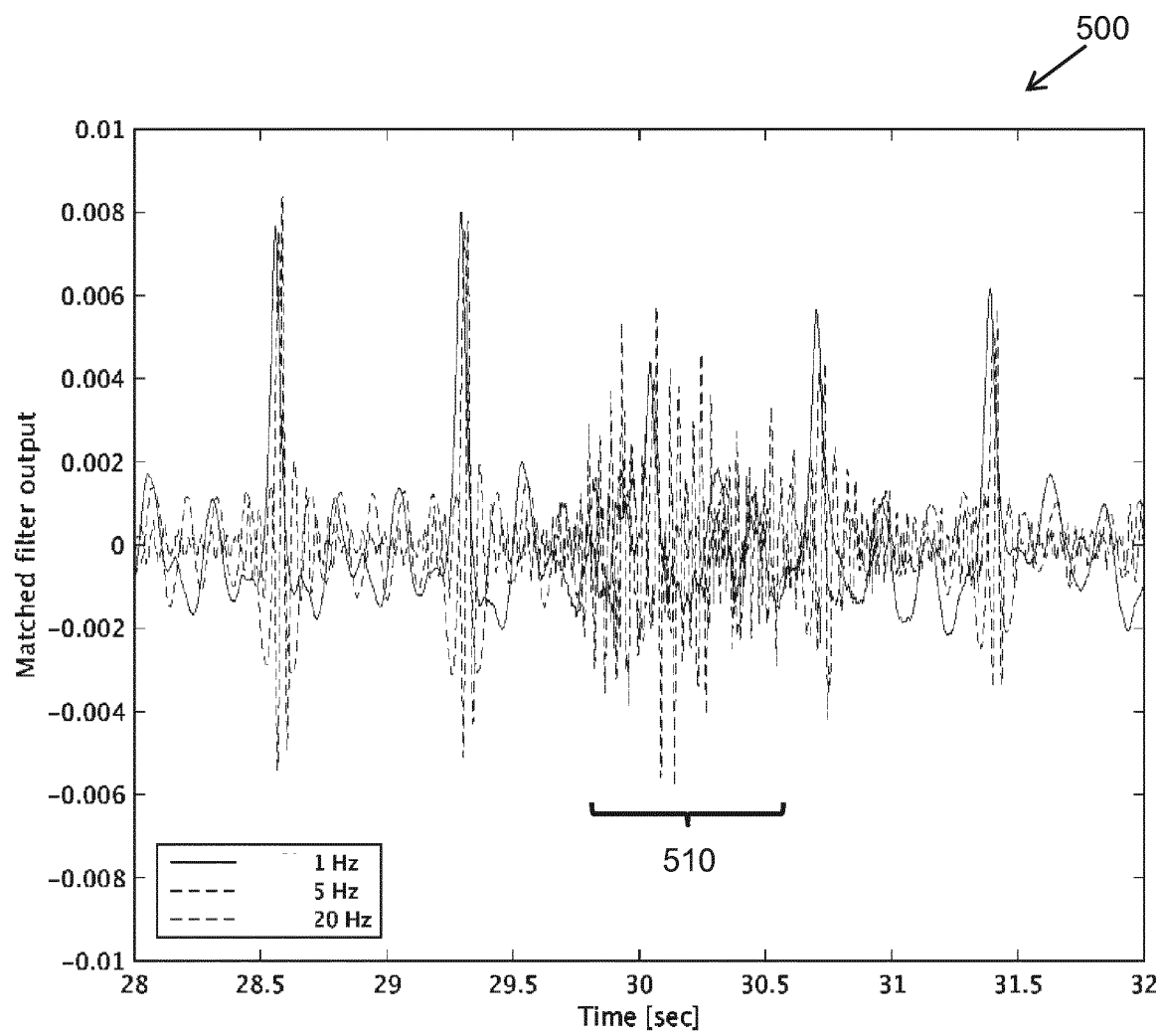
FIGS. 5A to 5D show three enhanced ECG signals corresponding to the three ECG templates shown in FIGS. 4A to 4D.
Figure 5B:
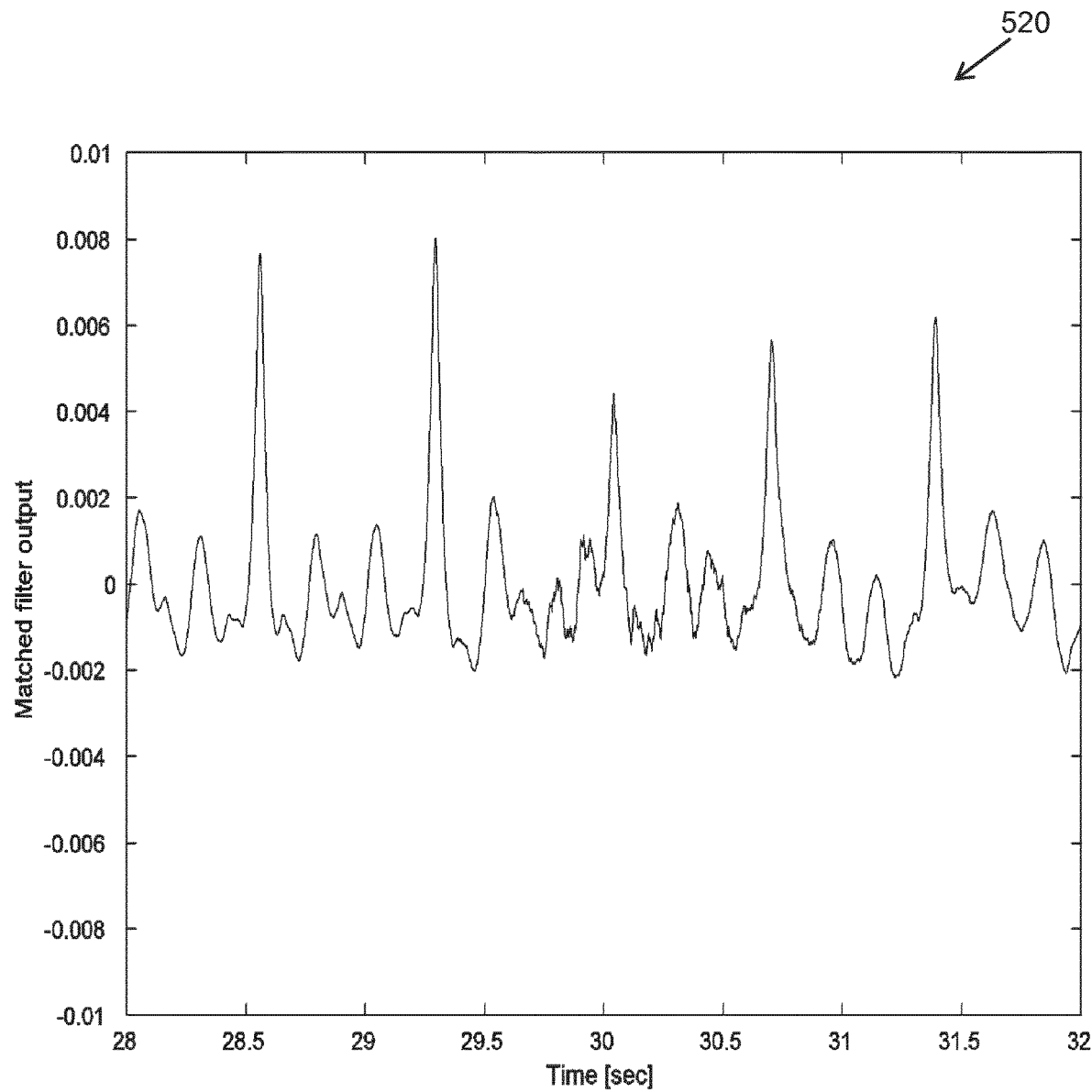
Figure 5C:
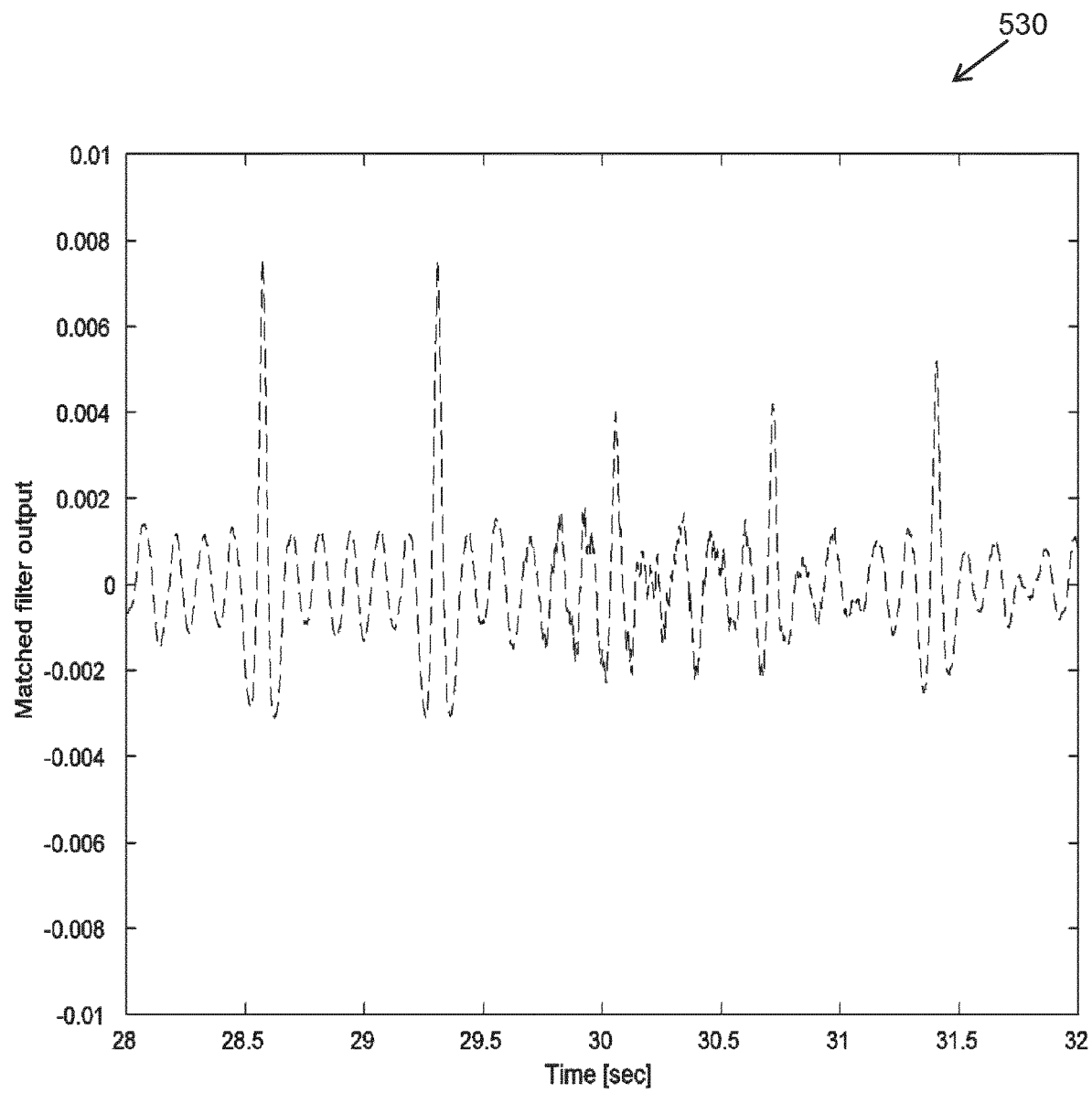
Figure 5D:
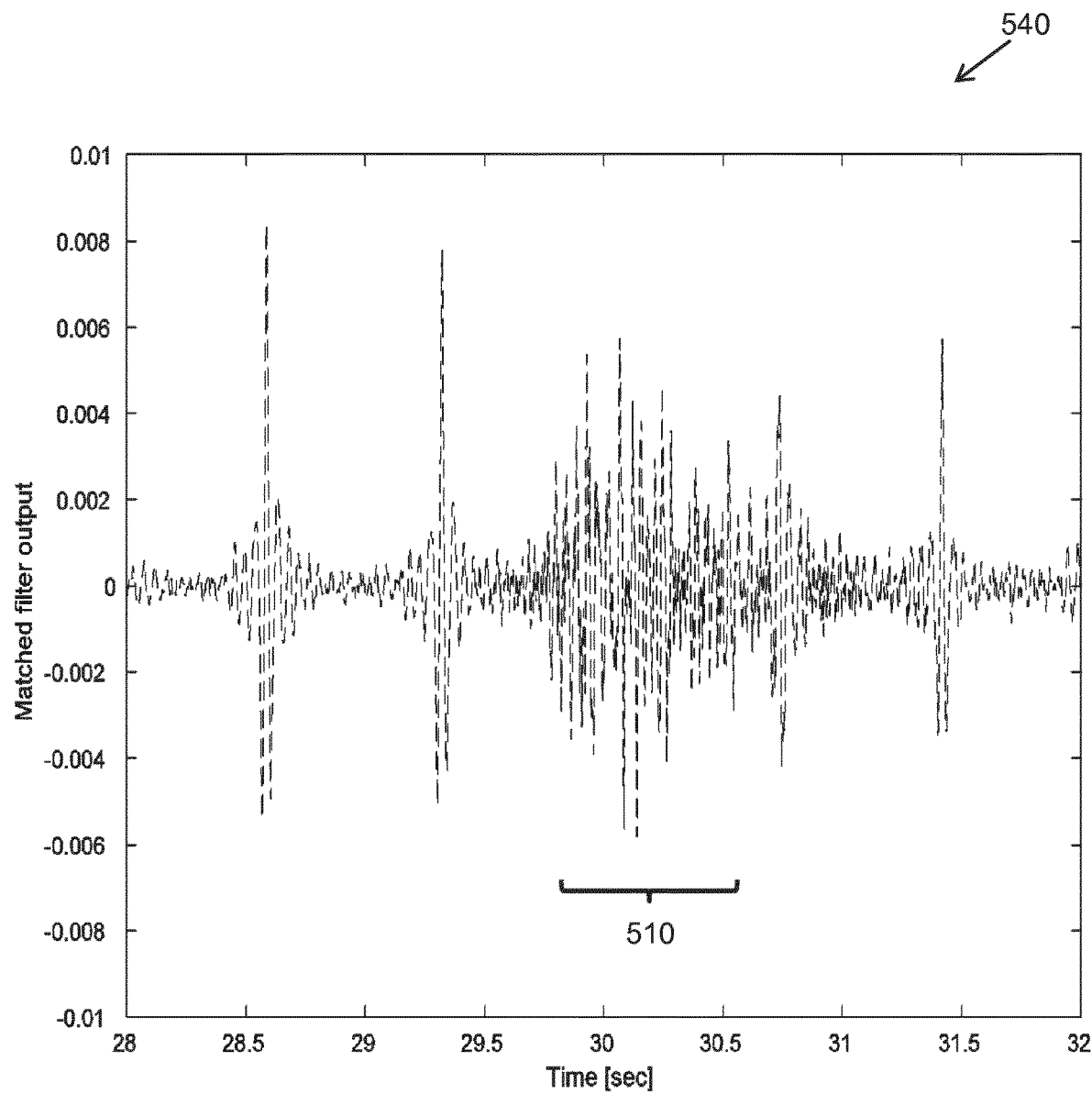

FIG. 5A shows a graph 500 of the enhanced ECG signal that is generated by filtering the high pass filtered combined signal with each of the ECG templates shown in FIG. 4A. As before, FIGS. 5B to 5D show the separated plots of FIG. 5A. FIG. 5B shows a graph 520 of an enhanced ECG signal corresponding to the ECG template of FIG. 4B with a first high pass filter having a cutoff frequency of 1 Hz. FIG. 5C shows a graph 530 of an enhanced ECG signal corresponding to the ECG template of FIG. 4C with a first high pass filter having a cutoff frequency of 5 Hz. FIG. 5D shows a graph 540 of an enhanced ECG signal corresponding to the ECG template of FIG. 4D with a first high pass filter having a cutoff frequency of 20 Hz.

In this case, the high pass filtered combined signal consists of five heart cycles and one maximum inspiratory maneuver, which occurs at around 30 seconds. It can be seen in FIGS. 5A and 5D that the ECG template for a first high pass filter with a cutoff frequency of 20 Hz, as shown in FIGS. 4A and 4D, results in an enhanced ECG signal that is not usable for the detection of the peak of the heart cycle that is present at the moment of the maximum inspiratory maneuver due to the large amount of noise 510 in the signal. Using ECG templates with a first high pass filter with a cutoff frequency of 1 Hz and 5 Hz gives an enhanced ECG signal that has a much better signal to noise ratio that allows for the detection of all heart cycle peaks, even during the maximum inspiratory maneuver.

Figure 6A:
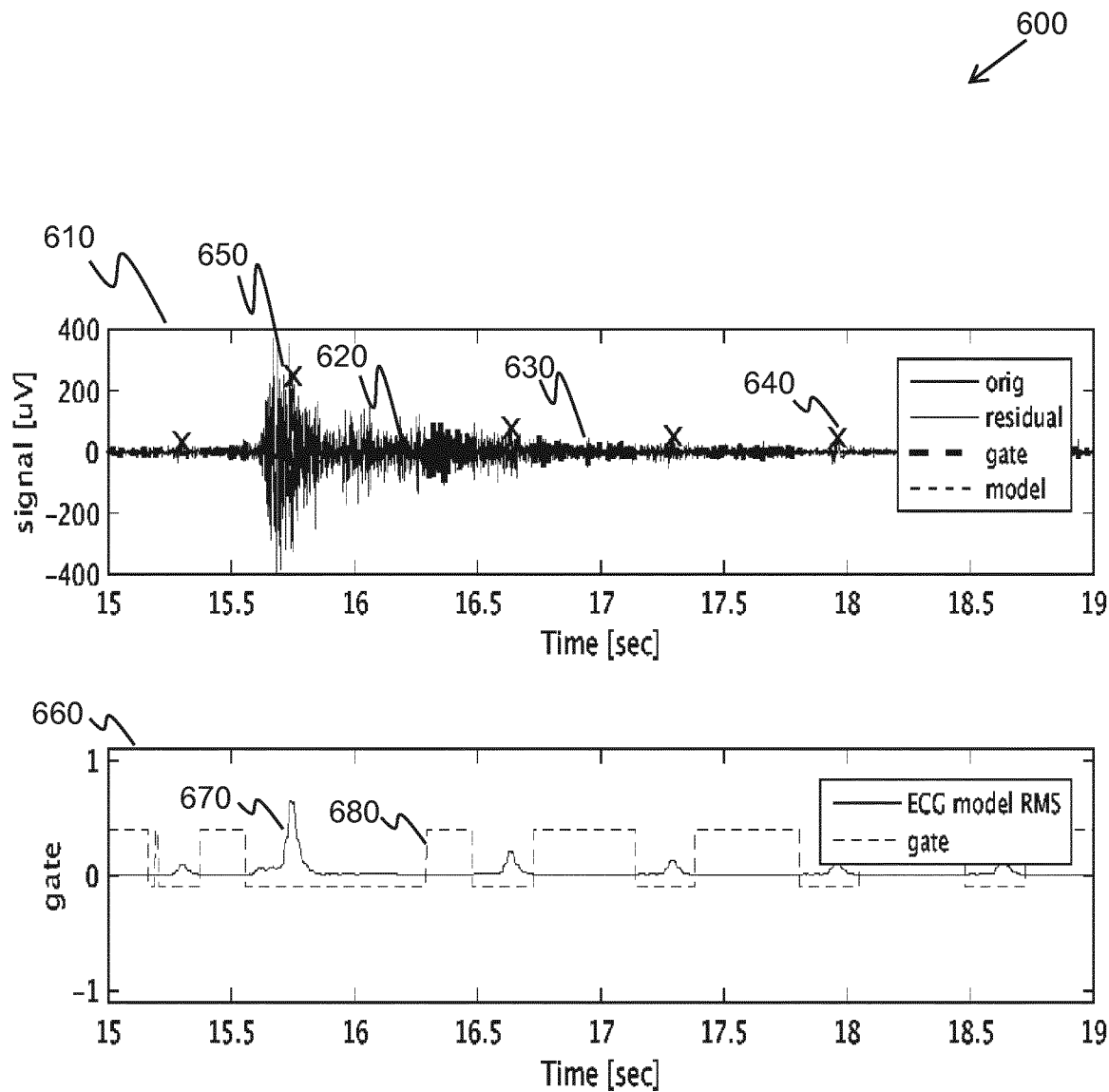
FIGS. 6A and 6B show the second EMG signal, the second ECG model signal, the filtered EMG signal, the RMS of the second ECG model signal and the gate signal for a first high pass filter with cutoff frequency of 20 Hz and without applying a second high pass filter.
Figure 6B:
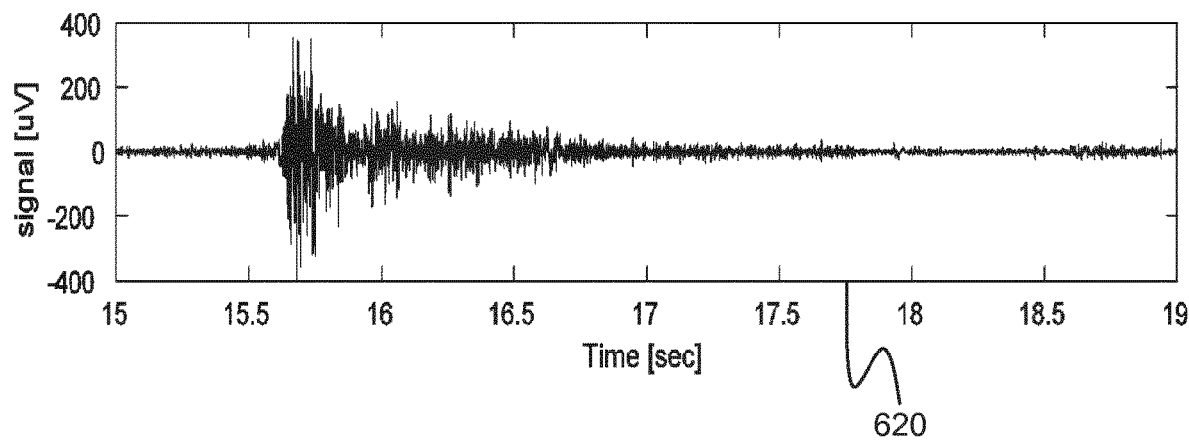
Figure 6B:
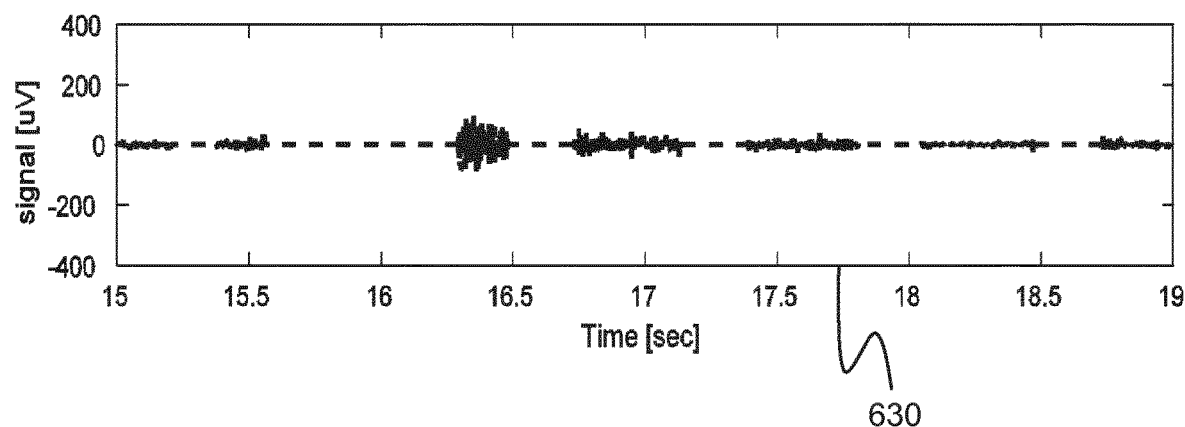
Figure 6B:
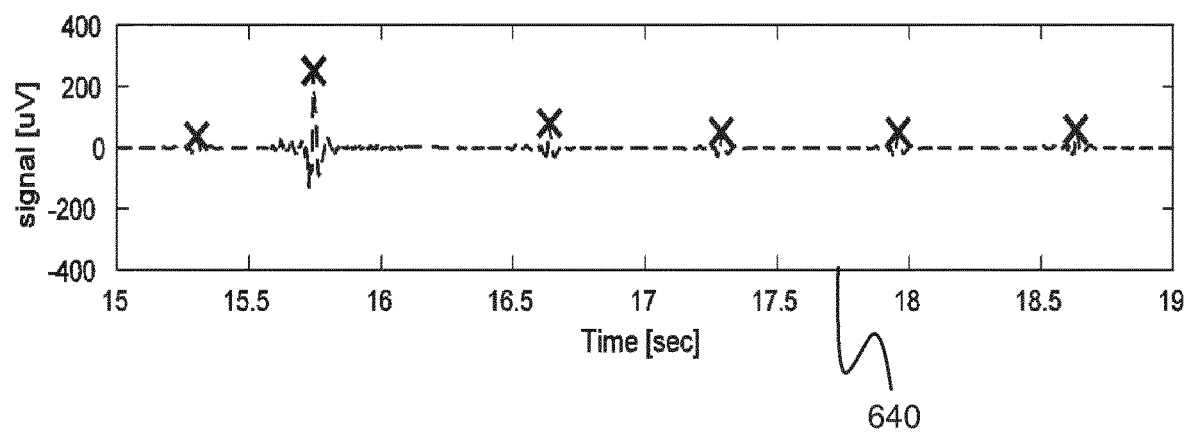

FIG. 6A shows two graphs 600, the first graph 610 representing the second EMG signal 620, the gated second EMG signal 630 and the second ECG model signal with the R-peaks 640. For the purposes of clarity, FIG. 6B shows the separated plots of the first graph. The second ECG model signal is generated by way of a first high pass filter with a cutoff frequency of 20 Hz and the second high pass filter has not yet been applied. In this graph 610 there is a single erroneous R-peak 650.

The second graph 660 in FIG. 6A shows the RMS of the second ECG model signal 670 and the gate signal 680. Due to the erroneous R-peak 650, there is too much gating, resulting in too much energy gated from the second EMG signal 620 as can be seen in the gated second EMG signal 630.

Figure 7A:
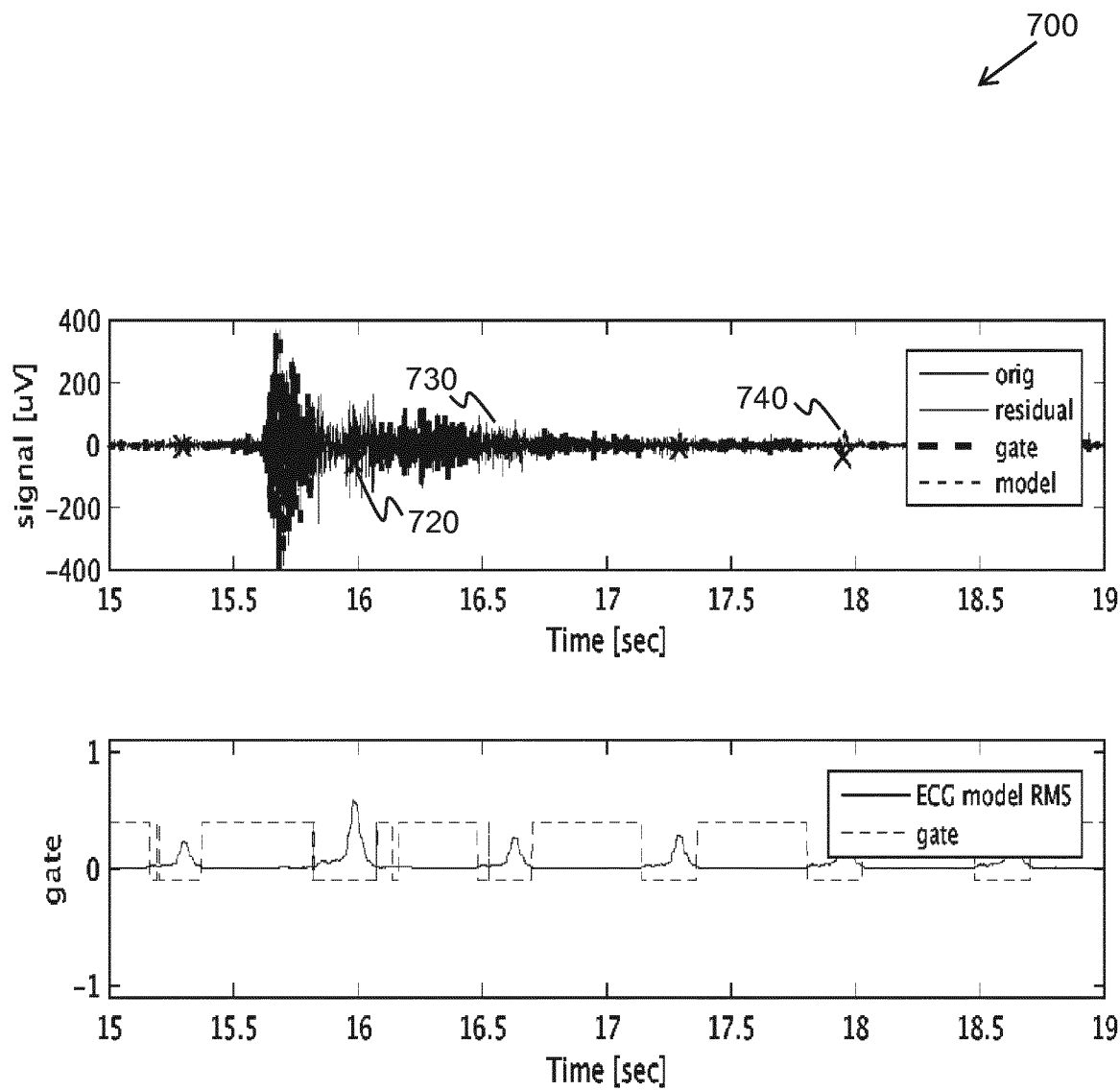
FIGS. 7A and 7B show the plots of FIGS. 6A and 6B for a first high pass filter with cutoff frequency of 5 Hz and a second high pass filter with cutoff frequency of 20 Hz.
Figure 7B:
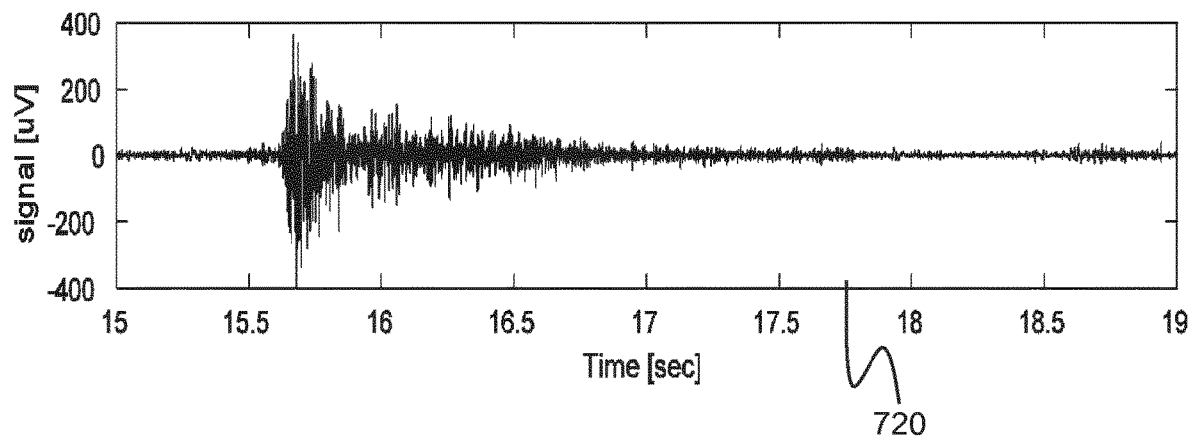
Figure 7B:
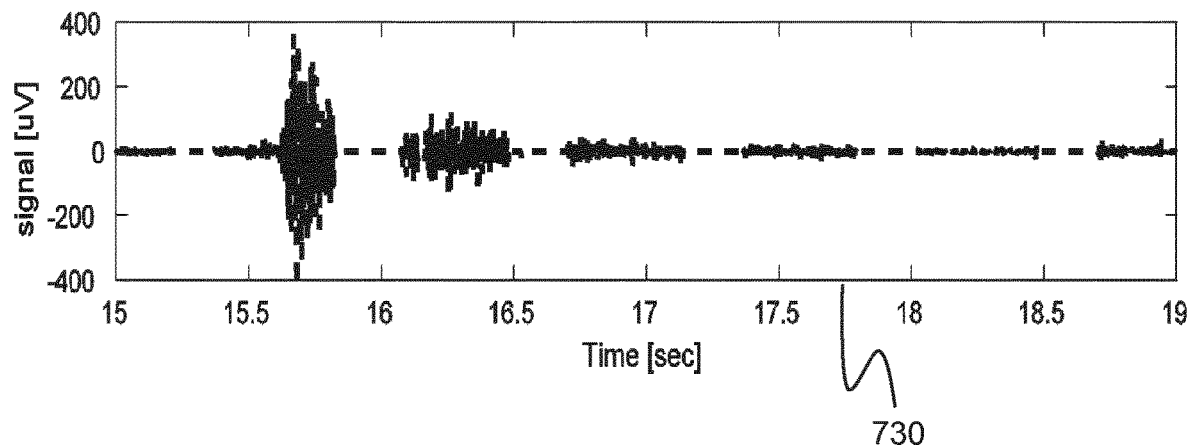
Figure 7B:
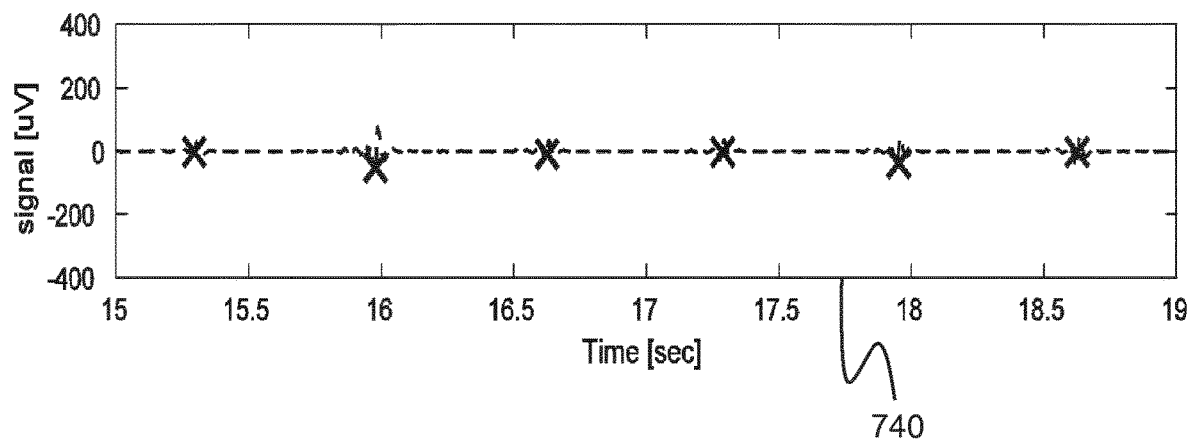

FIG. 7A shows two graphs 700 similar to the graphs 600, again with the first graph 710 representing the second EMG signal 720, the gated second EMG signal 730 and the second ECG model signal with the R-peaks 740; however, the cutoff frequency of the first high pass filter has been lowered to 5 Hz, thereby preserving the T-waves of the ECG signals to be used in the generation of the ECG model signal. FIG. 7B shows the separated plots of the first graph of FIG. 7A.

As a result of the lower cutoff frequency, and so the additional ECG energy in the matched filter, all of the R-peaks 740 are correctly detected. The cutoff frequency of the second high pass filter has been set to 20 Hz and using the second ECG model signal in the gating technique, the gating of the second EMG signal 720 is improved to more optimally remove the residual ECG from the EMG signal.

Figure 8A:
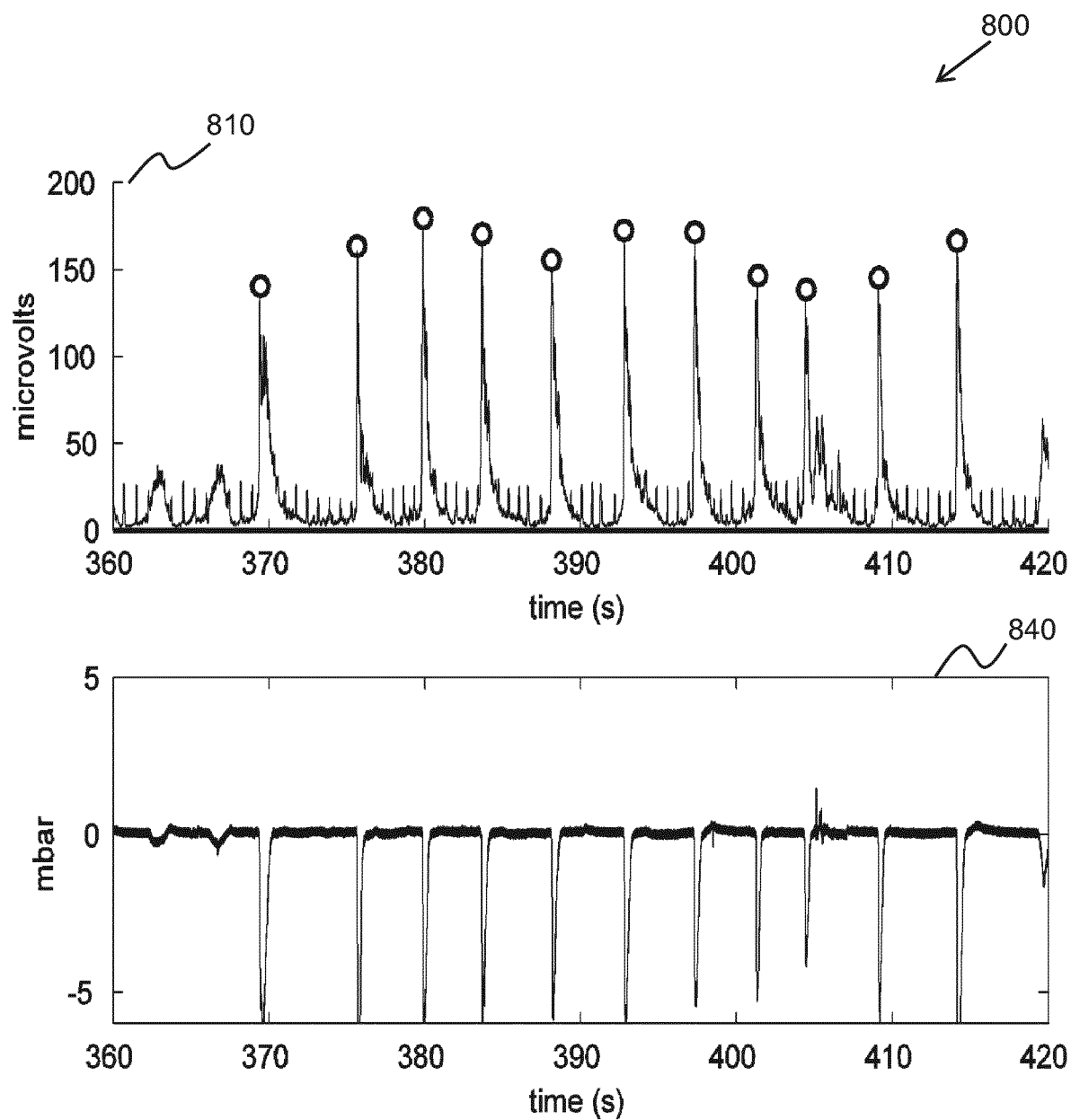
FIGS. 8A to 8C show comparisons between manual and two automated sniff detection methods.

FIG. 8A shows two graphs 800, the first graph 810 representing the RMS signal of the high pass filtered combined signal, wherein the first high pass filter has a cutoff frequency of 20 Hz. In this case, the second high pass filter has not been applied. The second graph 840 shows a plot of pressure against time, collected by way of a nasal cannula, in order to indicate inhalations corresponding to the peaks of the EMG signal.

As can be seen from both the first 810 and second 840 graphs, the first two breaths in this window are quiet breaths, where the SNR is reasonably high. However, the next 11 breaths are sniffs, where the patient tries to perform a maximum inspiratory maneuver. The hollow markers (circles) in the first graph 810 are the sniff annotations performed by a clinician.

Figure 8B:
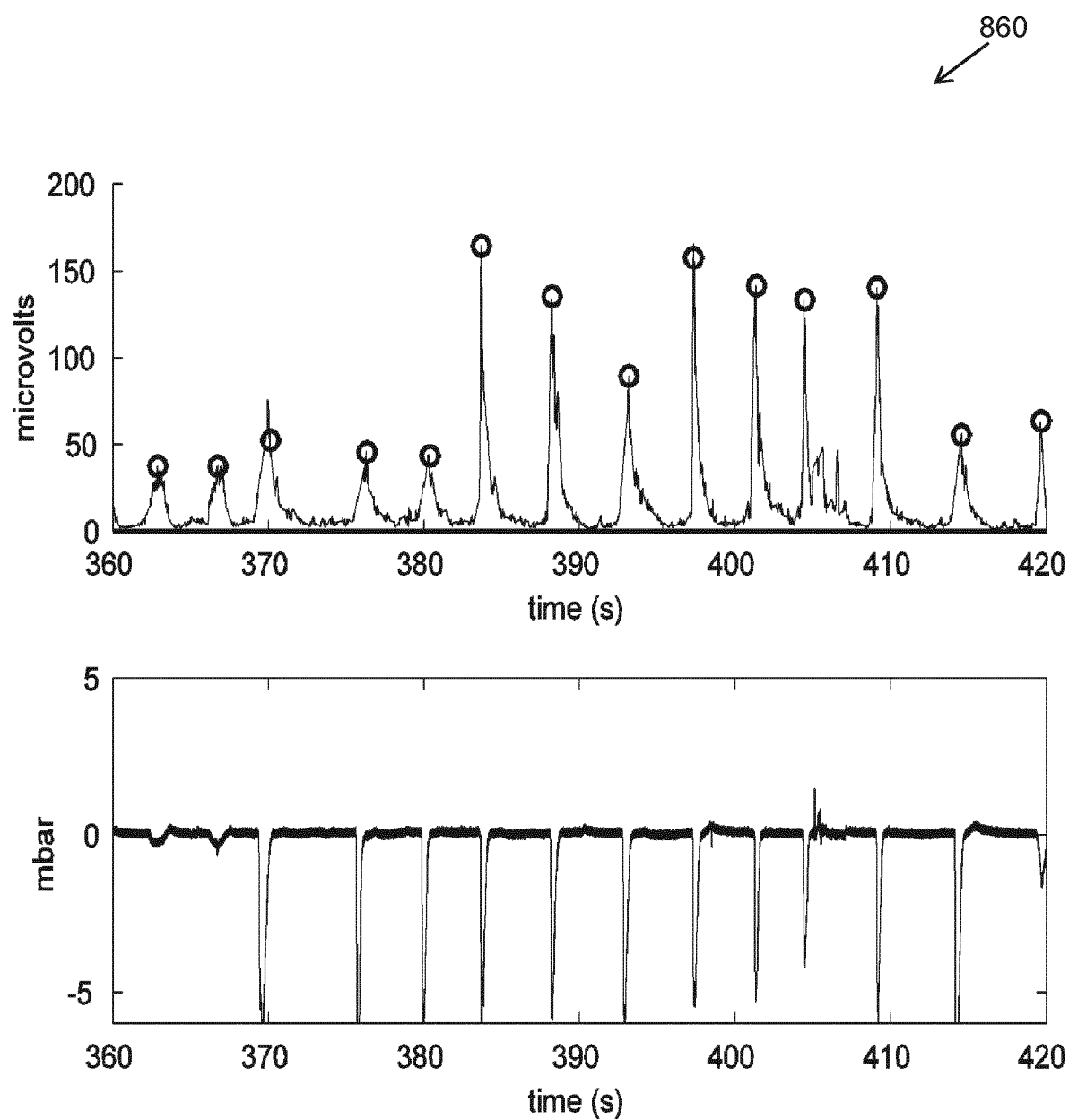
Figure 8C:
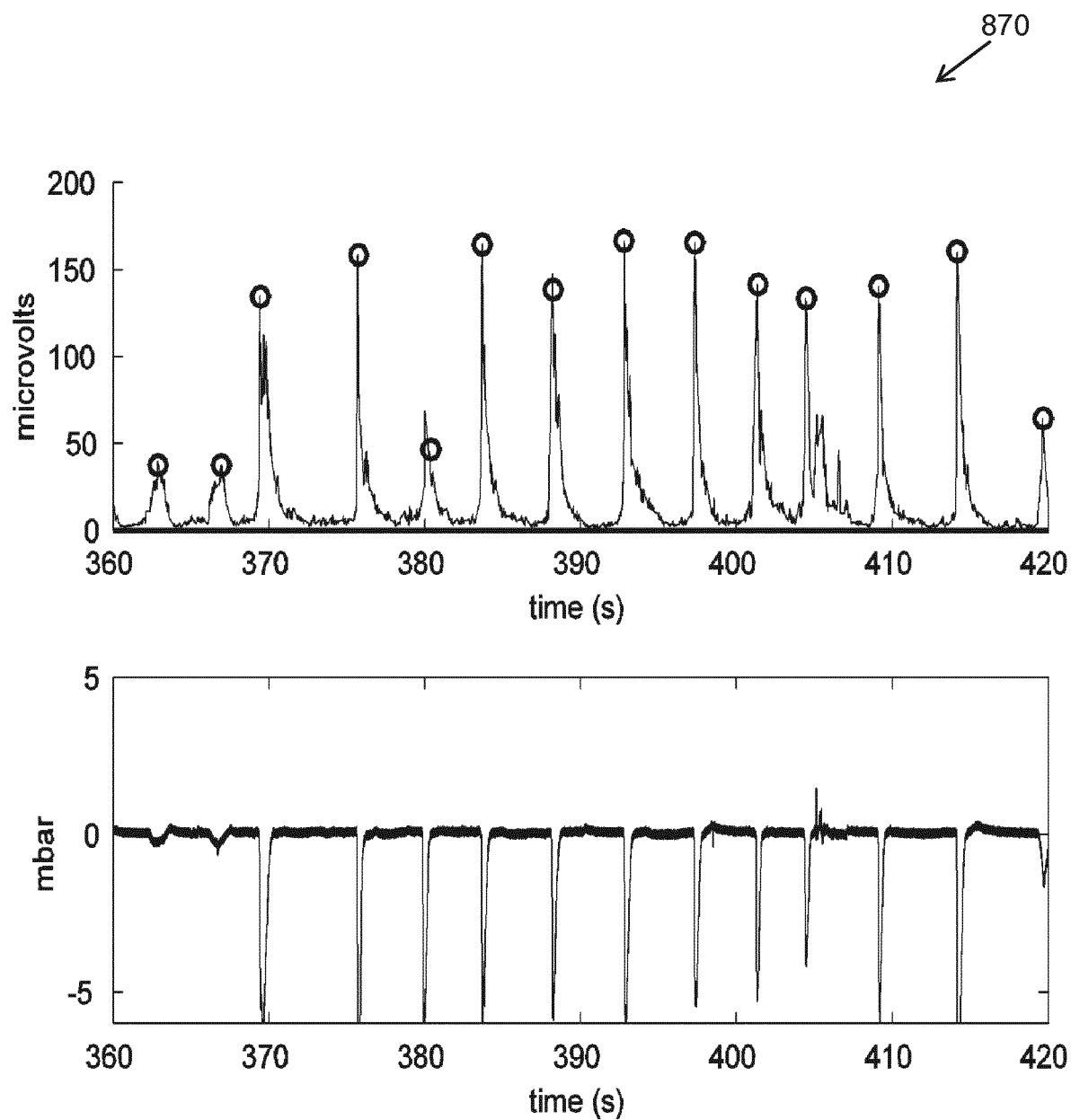

FIGS. 8B and 8C depict similar graphs, 860 and 870, where the hollow markers (circles) now represent sniffs detected automatically by the algorithm described above. For FIG. 8B, a first high pass filter with a cutoff frequency of 20 Hz is used and the second high pass filter has not been applied. For FIG. 8C, a first high pass filter with a cutoff frequency of 5 Hz and a second high pass filter a cutoff frequency of 20 Hz are used.

Comparing FIG. 8B to FIG. 8A, the disparity between the locations of the markers indicates that the energy of many of the sniffs is attenuated due to poor R-peak detection.

Looking to FIG. 8C from FIG. 8A, it is clear to see that selecting the cutoff frequency of the first high pass filter to be 5 Hz, thereby preserving the T-waves of the ECG signals to be used in the generation of the ECG model signal, leads to a significant improvement in the accuracy of the automatically detected sniffs.

The sequence of processing steps given above is purely by way of example.

For example, any high pass filter operation may be implemented by a band pass filter, in that there will be a highest frequency region which is not of interest and can thus also be filtered.

The different signal processing steps are explained above to make the operation of the method and system clear. In practice, the raw EMG signal will first be digitized and then all subsequent signal processing is implemented by a digital signal processing system. In such signal processing, the different processing steps are not necessarily individually distinguishable. Furthermore, some of the signal processing functions are optional.

The invention is of particular interest for EMG signals which may be contaminated by ECG signals, hence EMG signals associated with skeletal muscles in the vicinity of the heart. Of most interest is the muscles that control diaphragm movement, and hence relate to breathing.

As discussed above, embodiments make use of a signal processing unit. The signal processing unit can be implemented in numerous ways, with software and/or hardware, to perform the various functions required. A processor is one example of a controller which employs one or more microprocessors that may be programmed using software (e.g., microcode) to perform the required functions. A controller may however be implemented with or without employing a processor, and also may be implemented as a combination of dedicated hardware to perform some functions and a processor (e.g., one or more programmed microprocessors and associated circuitry) to perform other functions.

Examples of controller components that may be employed in various embodiments of the present disclosure include, but are not limited to, conventional microprocessors, application specific integrated circuits (ASICs), and field-programmable gate arrays (FPGAs).

In various implementations, a processor or controller may be associated with one or more storage media such as volatile and non-volatile computer memory such as RAM, PROM, EPROM, and EEPROM. The storage media may be encoded with one or more programs that, when executed on one or more processors and/or controllers, perform the required functions. Various storage media may be fixed within a processor or controller or may be transportable, such that the one or more programs stored thereon can be loaded into a processor or controller.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A method for generating a filtered EMG signal, the method comprising:
    obtaining a combined signal, wherein the combined signal comprises an ECG signal and an EMG signal;
    applying a first high pass filter to the combined signal;
    generating an ECG model signal based on the high pass filtered combined signal;
    generating a first EMG signal based on at least one of the ECG model signal and the high pass filtered combined signal;
    applying a second high pass filter to the first EMG signal to generate a second EMG signal and to the ECG model signal to generate a second ECG model signal;
    generating the filtered EMG signal based on the second EMG signal and the second ECG model by way of a gating technique; and
    generating a clinical parameter from the generated filtered EMG signal;
    wherein the gating technique comprises:
    computing the root mean square, RMS, of the ECG model signal;
    computing a binary gating signal based on the RMS of the ECG model signal; and
    gating the second EMG signal using the binary gating signal.

2. A method as claimed in claim 1, wherein the first high pass filter has a cutoff frequency of less than or equal to 5 Hz.

3. A method as claimed in claim 1, wherein the second high pass filter has a cutoff frequency of greater than or equal to 20 Hz.

4. A method as claimed in claim 1, wherein the generating of the ECG model signal comprises:

generating an enhanced ECG signal by applying a matched filter to the high pass filtered combined signal, wherein the matched filter uses an ECG template;

identifying peaks in the enhanced ECG signal;

identifying fiducial points in the high pass filtered combined signal based on the peaks from the enhanced ECG signal; and generating an ECG model signal based on the high pass filtered combined signal and the fiducial points.

5. A method as claimed in claim 4, wherein the fiducial points comprise R-peaks.

6. A method as claimed in claim 1, wherein the generating of the ECG model signal further comprises tapering between each ECG cycle in the ECG model signal.

7. A method as claimed in claim 4, wherein the generating of the ECG model signal further comprises:

computing an ECG template using a single ECG cycle of the ECG model signal; and providing the computed ECG template to the matched filter.

8. A controller for generating a filtered EMG signal in an EMG measurement system, wherein the controller is adapted to:

obtain a combined signal, wherein the combined signal comprises an ECG signal and an EMG signal;

apply a first high pass filter to the combined signal;

generate an ECG model signal based on the high pass filtered combined signal;

generate a first EMG signal based on at least one of the high pass filtered combined signal and the ECG model signal;

apply a second high pass filter to the first EMG signal to generate a second EMG signal and to the ECG model signal to generate a second ECG model signal; and generate the filtered EMG signal based on the second EMG signal and the second ECG model by way of a gating technique; and generate a clinical EMG parameter from the generated filtered EMG signal;

wherein the gating techniques comprises:

computing the root mean square, RMS, of the ECG model signal;

computing a binary gating signal based on the RMS of the ECG model signal; and gating the second EMG signal using the binary gating signal.

9. A method as claimed in claim 1, wherein the generating of the first EMG signal comprises generating a partially filtered EMG signal by subtracting the ECG model signal from the high pass filtered combined signal.

10. A method as claimed in claim 1, wherein the method further comprises generating a continuous RMS of the filtered EMG signal, wherein the generating of the continuous RMS of the filtered EMG signal comprises:

estimating a signal level of a non-gated region close to a gate boundary of the filtered EMG signal;

generating a continuous filtered EMG signal by interpolating values in a gated region of the filtered EMG signal based on the estimated signal levels; and computing the RMS of the continuous filtered EMG signal.

11. A method as claimed in claim 1, wherein the method further comprises, after applying the first high pass filter, buffering the high pass filtered combined signal.

12. A method as claimed in claim 11, wherein the buffering is performed over a time period of between 30 seconds and 5 minutes.

13. A computer program comprising computer program code means which is adapted, when said computer program is run on a computer, to implement the method of claim 1.

14. A controller for generating a filtered EMG signal in an EMG measurement system, wherein the controller is adapted to:

obtain a combined signal, wherein the combined signal comprises an ECG signal and an EMG signal;

apply a first high pass filter to the combined signal;

generate an ECG model signal based on the high pass filtered combined signal;

generate a first EMG signal based on at least one of the high pass filtered combined signal and the ECG model signal;

apply a second high pass filter to the first EMG signal to generate a second EMG signal and to the ECG model signal to generate a second ECG model signal; and generate the filtered EMG signal based on the second EMG signal and the second ECG model by way of a gating technique; and generate a clinical EMG parameter from the generated filtered EMG signal;

wherein the gating techniques comprises:

computing the root mean square, RMS, of the ECG model signal;

computing a binary gating signal based on the RMS of the ECG model signal; and gating the second EMG signal using the binary gating signal.

15. An EMG measurement system comprising:

a controller as claimed in claim 14;

an EMG electrode adapted to measure the combined signal; and a signal output device for outputting the filtered EMG signal.

16. A method as claimed in claim 1, wherein the clinical parameter comprises a respiratory function metric.

17. A method as claimed in claim 1, wherein the clinical parameter comprises neural respirator drive (NRD).

18. A controller as claimed in claim 14, wherein the clinical parameter comprises a respiratory function metric.

19. A controller as claimed in claim 14, wherein the clinical parameter comprises neural respirator drive (NRD).

* * * * *